United States Patent
Casanovas Casanovas et al.

(10) Patent No.: US 11,802,874 B2
(45) Date of Patent: Oct. 31, 2023

(54) PD-ECGF AS BIOMARKER OF CANCER

(71) Applicants: FUNDACIÓ INSTITUT D'INVESTIGACIÓ BIOMÈDICA DE BELLVITGE (IDIBELL), Hospitalet de Llobregat (ES); INSTITUT CATALÀ D'ONCOLOGIA (ICO), L'Hospitalet de Llobregat (ES)

(72) Inventors: Oriol Casanovas Casanovas, Barcelona (ES); Gabriela Jiménez Valerio, Barcelona (ES); María Ochoa De Olza, Sant Cugat del Vallès (ES); Valentí Navarro Pérez, Sabadell (ES); Nicklas Bassani, Barcelona (ES); Helena Verdaguer, Barcelona (ES)

(73) Assignees: FUNDACIO INSTITUT D'INVESTIGACIÓ BIOMÈDICA DE BELLVITGE (IDIBELL), Hospitalet de Llobregat (ES); INSTITUT CATALÀ D'ONCOLOGIA (ICO), L'Hospitalet de Llobregat (ES)

( * ) Notice: Subject to any disclaimer, the term of this patent is extended or adjusted under 35 U.S.C. 154(b) by 0 days.

(21) Appl. No.: 15/556,568

(22) PCT Filed: Mar. 10, 2016

(86) PCT No.: PCT/EP2016/055143
§ 371 (c)(1),
(2) Date: Sep. 7, 2017

(87) PCT Pub. No.: WO2016/142471
PCT Pub. Date: Sep. 15, 2016

(65) Prior Publication Data
US 2018/0052164 A1 Feb. 22, 2018

(30) Foreign Application Priority Data
Mar. 11, 2015 (EP) .................... 15382109

(51) Int. Cl.
G01N 33/574 (2006.01)

(52) U.S. Cl.
CPC . *G01N 33/57415* (2013.01); *G01N 33/57419* (2013.01); *G01N 33/57438* (2013.01); *G01N 2333/475* (2013.01); *G01N 2800/52* (2013.01)

(58) Field of Classification Search
CPC ....... G01N 33/57415; G01N 33/57419; G01N 33/57438; G01N 2333/475; G01N 2800/52; G01N 33/57484; G01N 33/6893
See application file for complete search history.

(56) References Cited

U.S. PATENT DOCUMENTS

| | | | |
|---|---|---|---|
| 5,798,213 A | 8/1998 | Miyadera et al. | |
| 7,611,839 B2 | 11/2009 | Twine et al. | |
| 8,029,981 B2 | 10/2011 | Nakamura et al. | |
| 8,110,675 B2 | 2/2012 | Chen et al. | |
| 10,364,466 B2* | 7/2019 | Bais ................. | G01N 33/574 |
| 2013/0178383 A1* | 7/2013 | Spetzler ............ | G01N 33/5432 506/9 |

FOREIGN PATENT DOCUMENTS

| | | |
|---|---|---|
| CN | 101993919 A | 3/2011 |
| EP | 0749981 A1 | 12/1996 |
| EP | 1510588 A1 | 3/2005 |
| WO | 2003086299 A2 | 10/2003 |
| WO | 2007115376 A1 | 10/2007 |
| WO | 2012129448 A1 | 9/2012 |

OTHER PUBLICATIONS

Enomoto et al. Variations in the expression of platelet-derived endothelial cell growth factor in human colorectal polyps. Surgery Today 30: 711-717, 2000.*
Enomoto et al. (Surg. Today 30: 711-717, 2000).*
Office Action for Japanese Application 2017-548041, dated Nov. 26, 2019, 9 pages.
Yamamoto et al., "Prediction of the effect of 5'-deoxy-5-fluorouridine by the status of angiogenic enzyme thymidine phosphorylase expression in recurrent breast cancer patients", Oncology Reports, 1996, pp. 863-865, vol. 3.
Akizawa et al., "In Vitro and In Vivo Evaluations of a Radioiodinated Thymidine Phosphorylase Inhibitor as a Tumor Diagnostic Agent for Angiogenic Enzyme Imaging", Nuclear Medicine and Biology, 2010, pp. 427-432, vol. 37.
Balzarini et al., "7-Deazaxanthine, a Novel Prototype Inhibitor of Thymidine Phosphorylase", FEBS Letters, 1998, pp. 91-95, vol. 438.
Batchelor et al., "AZD2171, a Pan-VEGF Receptor Tyrosine Kinase Inhibitor, Normalizes Tumor Vasculature and Alleviates Edema in Glioblastoma Patients", Cancer Cell, Jan. 2007, pp. 83-95, vol. 11, No. 1.

(Continued)

*Primary Examiner* — Alana Harris Dent
(74) *Attorney, Agent, or Firm* — Thompson Coburn LLP; William A. Holtz

(57) ABSTRACT

The present invention corresponds to the field of cancer and is related to predicting cancer detection, diagnosis, monitoring and prediction of response to treatment, in particular platelet derived-endothelial cell growth factor (PD-ECGF) levels for their use as a potential value in monitoring disease evolution and predicting response to anti-angiogenic treatment.

15 Claims, 23 Drawing Sheets

(56) References Cited

OTHER PUBLICATIONS

Bouïs et al., "Combination of Vascular Endothelial Growth Factor (VEGF) and Thymidine Phosphorylase (TP) to Improve Angiogenic Gene Therapy", Angiogensis, 2003, pp. 185-192, vol. 6.

Brennan et al., "The Somatic Genomic Landscape of Glioblastoma", Cell, Oct. 10, 2013, pp. 462-477, vol. 155, No. 2.

Bronckaers et al., "The Dual Role of Thymidine Phosphorylase in Cancer Development and Chemotherapy", Medicinal Research Reviews, 2009, pp. 903-953, vol. 29, No. 6.

Brostjan et al., "Monitoring of Circulating Angiogenic Factors in Dendritic Cell-Based Cancer Immunotherapy", Cancer, Nov. 15, 2003, pp. 2291-2301, vol. 98, No. 10.

Clark, "Prognostic Factors Versus Predictive Factors: Examples From a Clinical Trial of Erlotinib", Molecular Oncology, 2008, pp. 406-412, vol. 1.

Elamin et al., "Thymidine Phosphorylase in Cancer; Enemy or Friend?", Cancer Microenvironment, Aug. 1, 2015.

European Search Report for EP Application 15382109.5 dated Sep. 3, 2015.

Fan et al., "Chronic Exposure of Colorectal Cancer Cells to Bevacizumab Promotes Compensatory Pathways that Mediate Tumour Cell Migration", British Journal of Cancer, 2011, pp. 1270-1277, vol. 104.

Fischer et al., "Anti-PIGF Inhibits Growth of VEGF(R)-Inhibitor-Resistant Tumors without Affecting Healthy Vessels", Cell, Nov. 2, 2007, pp. 463-475, vol. 131.

Fujimoto et al., "Expression of Platelet-Derived Endothelial Cell Growth Factor (PD-ECGF) and its mRNA in Uterine Cervical Cancers", British Journal of Cancer, Mar. 1, 1999, pp. 1249-1254, vol. 79, No. 7/8.

Fukushima et al., "Structure and Activity of Specific Inhibitors of Thymidine Phosphorylase to Potentiate the Function of Antitumor 2'-Deoxyribonucleosides", Biochemical Pharmacology, 2000, pp. 1227-1236, vol. 59.

Grierson et al., "Synthesis and In Vitro Evaluation of 5-Fluro-6-[(2-Iminopyrrolidin-1-YL)Methyl]Uracil, TPI(F): An Inhibitor of Human Thymidine Phosphorylase (TP)", Nucleosides, Nucleotides, and Nucleic Acids, 2010, pp. 49-54, vol. 29.

Hussain et al., "An Investigation of the Kinetic and Anti-Angiogenic Properties of Plant Glycoside Inhibitors of Thymidine Phosphorylase", Journal of Asian Natural Products Research, Feb. 2009, pp. 159-167, vol. 11, No. 2.

International Search Report and Written Opinion for PCT/EP2016/055143 dated Apr. 26, 2016.

Italiano, "Prognostic or Predictive? It's Time to Get Back to Definitions!", Journal of Clinical Oncology, Dec. 10, 2011, pp. 4718-4724, vol. 29, No. 35.

Jain et al., "The Role of Phosphate in the Action of Thymidine Phosphorylase Inhibitors: Implications for the Catalytic Mechanism", Bioorganic & Medicinal Chemistry Letters, 2010, pp. 1648-1651, vol. 20.

Kim et al., "Overcoming Evasive Resistance from Vascular Endothelial Growth Factor A Inhibition in Sarcomas by Genetic or Pharmacologic Targeting of Hypoxia-Inducible Factor 1a", International Journal of Cancer, 2013, pp. 29-41, vol. 132.

Liekens et al., "The Nucleoside Derivative 5'-O-Trityl-inosine (KIN59) Suppresses Thymidine Phosphorylase-triggered Angiogenesis via a Noncompetitive Mechanism of Action", The Journal of Biological Chemistry, Jul. 9, 2004, pp. 29598-29605, vol. 279, No. 28.

Lu et al., "Antiangiogenic and Antitumor Activity of 6-(2-Aminoethyl)Amino-5-Chlorouracil, a Novel Small-Molecule Inhibitor of Thymidine Phosphorylase, in Combination with the Vascular Endothelial Growth Factor-Trap", Clinical Cancer Research, Aug. 15, 2009, pp. 5136-5144, vol. 15, No. 16.

Mizutani et al., "Biomarkers in Renal Cell Carcinoma", Biotherapy, Jan. 1, 2009, pp. 150-157, vol. 23, No. 2.

Mizutani et al., "The Significance of Thymidine Phosphorylase/Platelet-Derived Endothelial Cell Growth Factor Activity in Renal Cell Carcinoma", Cancer, Aug. 1, 2003, pp. 730-736, vol. 98, No. 4.

Morita et al., "Quantitative Analysis of Thymidine Phosphorylase and Dihydropyrimidine Dehydrogenase in Renal Cell Carcinoma", Oncology, Aug. 1, 2003, pp. 125-131, vol. 65, No. 2.

Mulrane et al., "Automated Image Analysis in Histopathology: A Valuable Tool in Medical Diagnostics", Expert Review of Molecular Diagnostics, 2008, pp. 707-725, vol. 8, No. 6.

Oldenhuis et al., "Prognostic Versus Predictive Value of Biomarkers in Oncology", European Journal of Cancer, 2008, pp. 946-953, vol. 44.

Padrik et al., "Thymidine Phosphorylase as a Prognostic Factor in Renal Cell Carcinoma", International Urology and Nephrology, Jul. 2, 2009, pp. 295-298, vol. 42, No. 2.

Pula et al., "Proteomics Identifies Thymidine Phosphorylase as a Key Regulator of the Angiogenic Potential of Colony-Forming Units and Endothelial Progenitor Cell Cultures", Circulation Research, Jan. 2, 2009, pp. 32-40, vol. 104, No. 1.

Pérez-Pérez et al., "Thymidine Phosphorylase Inhibitors: Recent Developments and Potential Therapeutic Applications", Mini-Reviews in Medicinal Chemistry, 2005, pp. 1113-1123, vol. 5.

Rojo et al., "Review of Imaging Solutions for Integrated Quantitative Immunohistochemistry in the Pathology Daily Practice", Folia Histochemica Et Cytobiologica, 2009, pp. 349-354, vol. 47, No. 3.

Ruckhaberle et al., "Prognostic Impact of Thymidine Phosphorylase Expression in Breast Cancer Comparison of Microarray and Immunohistochemical Data", European Journal of Cancer, Feb. 1, 2010, pp. 549-557, vol. 46, No. 3.

Takahashi et al., "Platelet-Derived Endothelial Cell Growth Factor in Human Colon Cancer Angiogenisis: Role of Infiltrating Cells", Journal of the National Cancer Institute, Aug. 21, 1996, vol. 88, No. 16.

Takayama et al., "High Levels of Thymidine Phosphorylase as an Independent Prognostic Factor in Renal Cell Carcinoma", Japanese Journal of Clinical Oncology, Jul. 26, 2006, pp. 564-569, vol. 36, No. 9.

Taylor et al., "Integrative Genomic Profiling of Human Prostate Cancer", Cancer Cell, Jul. 13, 2010, pp. 11-22, vol. 18.

The Cancer Genome Atlas Research Network, "Comprehensive Molecular Characterization of Clear Cell Renal Cell Carcinoma", Nature, Jul. 4, 2013, pp. 43-49, vol. 499.

The Cancer Genome Atlas Research Network, Integrated Genomic Characterization of Papillary Thyroid Carcinoma, Cell, Oct. 23, 2014, pp. 676-690, vol. 159.

Toi et al., "Vascular Endothelial Growth Factor and Platelet-Derived Endothelial Cell Growth Factor Are Frequently Coexpressed in Highly Vascularized Human Breast Cancer", Clinical Cancer Research, Sep. 1995, pp. 961-964, vol. 1.

Toiyama et al., "Serum miR-21 as a Diagnostic and Prognostic Biomarker in Colorectal Cancer", Journal of the National Cancer Institute, Jun. 19, 2013, pp. 849-859, vol. 105, Issue 12.

Tsuji et al., "Platelet-Derived Endothelial Cell Growth Factor Expression is an Independent Prognostic Factor in Colorectal Cancer Patients After Curative Surgery", European Journal of Surgical Oncology, Apr. 1, 2004, pp. 296-302, vol. 30, No. 3.

Van Der Bilt et al., "Multiple VEGF Family Members are Simultaneously Expressed in Ovarian Cancer: A Proposed Model for Bevacizumab Resistance", Current Pharmaceutical Design, 2012, pp. 3784-3792, vol. 18.

Volm et al., "Cellular Predictive Factors for the Drug Response of Lung Cancer", Anti-Cancer Research—International Journal of Cancer Research and Treatment, Sep. 1, 2000, pp. 3449-3458, vol. 20, No. 5B.

Weng et al., "Inhibition of Thymidine Phosphorylase Expression by Using an HSP90 Inhibitor Potentiates the Cytotoxic Effect of Cisplatin in Non-Small-Cell Lung Cancer Cells", Biochemical Pharmacology, 2012, pp. 126-136, vol. 84.

Bhatt et al., "Cancer Biomarkers—Current Perspectives", Indian Journal of Medical Research, 2010, pp. 129-149, vol. 132.

Jain et al., "Biomarkers of Response and Resistance to Antiangiogenic Therapy", National Reviews Clinical Oncology, 2009, pp. 327-338, vol. 6, No. 6.

Manne et al., "Recent Advances in Biomarkers for Cancer Diagnosis and Treatment", Drug Discovery Today, 2005, pp. 965-976, vol. 10, No. 14.

(56) References Cited

OTHER PUBLICATIONS

Otrock et al., "Is VEGF a Predictive Biomarker to Anti-Angiogenic Therapy?", Critical Reviews in Oncology/Hematology, 2011, pp. 103-111, vol. 79.

Supplemental Technical Information filed with the Response to EP Communication, Dec. 17, 2018, 5 pages.

Vogelstein et al., "Cancer Genes and the Pathways They Control", Nature Medicine, 2004, pp. 789-799, vol. 10, No. 8.

"PharmaPoint: Renal Cell Carcinoma—Global Drug Forecast and Market Analysis to 2023", GlobalData, 2016, 321 pages.

Jahangiri et al., "Biomarkers Predicting Tumor Response and Evasion to Anti-Angiogenic Therapy", Biochimica et Biophysica Acta, 2012, pp. 86-100, vol. 1825.

Toi et al., "Significance of Thymidine Phosphorylase as a Marker of Protumor Monocytes in Breast Cancer", Clinical Cancer Research, 1999, pp. 1131-1137, vol. 5.

Zhao et al., "Relevance of PD—ECGF with Clinical Pathology and Prognosis of Renal Carcinoma", Jilin Medical Journal, 2012, 4 pages, vol. 33, No. 1.

Yibin, "The Expression of PD-ECGF, bFGF in Colorectal Cancer and Their Relationship with Microvessel Density (MVD)", Medical and Health Technology, 2006, 52 pages, No. 1.

Yonenaga et al., "The Expression of Thymidine Phosphorylase/Platelet-Derived Endothelial Cell Growth Factor is Correlated to Angiogenesis in Breast Cancer", Pathology, 1998, pp. 850-856, vol. 48.

Fujimoto et al., "The Value of Platelet-derived Endothelial Cell Growth Factor as a Novel Predictor of Advancement of Uterine Cervical Cancers", Cancer Research, Jul. 1, 2000, pp. 3662-3665, vol. 60.

Jin-No et al., "Circulating Platelet-Derived Endothelial Cell Growth Factor Increases in Hepatocellular Carcinoma Patients", Cancer, Apr. 1, 1998, pp. 1260-1267, vol. 82, No. 7.

Metzger et al., "High Basal Level Gene Expression of Thymidine Phosphorylase (Platelet-derived Endothelial Cell Growth Factor) in Coloreclal Tumors is Associated with Nonresponse to 5-Fluorouracil", Clinical Cancer Research, 1998, pp. 2371-2376, vol. 4.

Shimada et al., "Prognostic Significance of Serum Thymidine Phosphorylase Concentration in Esophageal Squamous Cell Carcinoma", American Cancer Society, Mar. 2022, pp. 1947-1954, vol. 94, No. 7.

* cited by examiner

HAZARD RADIO

|         | Mean  | Sd    | 2,50% | Median | 97,50% | P(HR>1) |
|---------|-------|-------|-------|--------|--------|---------|
| PD-ECGF | 0.708 | 0.151 | 0.457 | 0.697  | 1.034  | 0.041   |

Logrank Test P-Value: 9.48e-4

|  | # total cases | # cases relapsed | Median months disease free |
|---|---|---|---|
| Cases with alteration(s) in query gene | 18 | 2 | NA |
| Cases without alteration(s) in query gene | 296 | 11 | NA |

PD-ECGF AS BIOMARKER OF CANCER

CROSS-REFERENCE TO RELATED APPLICATIONS

This application is a U.S. National Phase application of PCT/EP2016/055143, filed on Mar. 10, 2016, claiming the benefit of European Application No. 15382109.5, filed Mar. 11, 2015, both of which are incorporated herein by reference in their entireties.

FIELD OF THE INVENTION

The present invention belongs to the field of cancer, particularly to biomarkers useful in cancer diagnosis and prognosis, wherein PD-ECGF biomarker modified levels in a sample from a subject are useful in diagnosing cancer in a subject or in prognosis of a subject suffering from cancer.

BACKGROUND OF THE INVENTION

The incidence of renal cell carcinoma (RCC) has been steadily rising each year. There have been significant advances described in our understanding of the biology of this cancer. Thanks to these advances, new therapeutic strategies in patients with advanced disease have been developed.

U.S. Pat. No. 8,029,981B2 relates to methods of diagnosing RCC that comprise determining the levels of the hypoxia-inducible protein-2 (HIG2). U.S. Pat. No. 7,611,839B2 relates to a method for confirming a diagnosis of RCC in a subject that comprises determining the levels of elongation factor 1 alpha 2 (EEF1A2) and toll-like receptor 2 (TLR2).

Nevertheless, there are still no biomarkers for routine use in the clinical practice in relation to RCC. Particularly in the last decade the methods used in prognosis of RCC have not changed. In general the therapy is classified by the histology; and patients continue to be exposed to potentially toxic therapies with no indication response probability. Therefore, there is still a need in the art for identifying potential biomarkers in the diagnosis and/or prognosis of RCC.

Worldwide, breast cancer is the second most common type of cancer (10.4%; after lung cancer) and the fifth most common cause of cancer death (after lung cancer, stomach cancer, liver cancer, and colon cancer). Among women worldwide, breast cancer is the most common cause of cancer death. The number of cases worldwide has significantly increased since the 1970s, a phenomenon partly blamed on modern lifestyles in the Western world. North American women have the highest incidence of breast cancer in the world.

Some well-established breast molecular markers with prognostic and/or therapeutic value include hormone receptors including estrogen receptor (ER) and progesterone receptor (PR), HER-2 oncogene, Ki-67, and p53. More recently identified molecular targets in breast cancer include CXCR4, caveolin and FOXP3.

With 655,000 deaths worldwide per year, colorectal cancer is the third most common form of cancer and the second leading cause of cancer-related death in the Western world. Many colorectal cancers are thought to arise from adenomatous polyps in the colon. These mushroom-shaped growths are usually benign, but some may develop into cancer over time. The majority of the time, the diagnosis of localized colon cancer is through colonoscopy.

Surgical resection is the primary treatment modality for early stage colorectal cancer (stage I through III), and the most powerful tool for assessing prognosis following potentially curative surgery is pathologic analysis of the resected specimen. Although the parameters that determine pathologic stage are the strongest predictors of postoperative outcome, other clinical, molecular, and histologic features may influence prognosis independent of stage. Among patients with stage IV disease, prognosis is more closely tied to the location and extent of distant metastatic disease Carcinoembryonic antigen (CEA) level is the tumor marker most often used in colorectal cancer. This level can be checked prior to surgery to predict prognosis, can be used during therapy to assess response to treatment or after completion of therapy to monitor for recurrence. CA 19-9 is a blood marker that may be elevated in colorectal cancer. MSI (microsatellite instability) can be used to identify early stage colon cancer that may require more aggressive treatment or to identify patients who should have further genetic testing due to the risk for a familial syndrome related to several cancer types. Recently, serum miR-21 has been proposed as an early diagnostic and prognostic biomarker in colorectal cancer (Toiyama et al. 2013 J. Natl. Cancer Inst. 105(12): 849-859).

However, due to the high incidence of both breast cancer and colorectal cancer, there is a continuing need in the art for diagnostic and/or predictive markers of response of said cancers.

SUMMARY OF THE INVENTION

The inventors have analyzed expression levels of PD-ECGF protein by inmunohistochemistry, ELISA and western blotting. PD-ECGF was not detected in non-cancerous tissue samples (0 in 12, 0%), but PD-ECGF protein was observed in 67 (>97%) tissue samples out of 69 RCC patients and in 10 (59%) out of 17 in tissue samples from breast cancer patients analyzed by inmunohistochemistry. Thus, PD-ECGF determination from tissue samples could be used for cancer detection, diagnosis or monitoring.

In addition, the inventors have found that PD-ECGF expression is a predictive factor of the response to anti-angiogenic therapies in patients with renal cell carcinoma, and colorectal cancer as shown by correlating PD-ECGF levels in the tumors prior to the initiation of the therapy with the risk of early progression (Kaplan-Meier and Gehan-Breslow-Wilcoxon tests, $p<0.045$). Therefore, PD-ECGF expression has potential value in predicting cancer progression to therapy as a predictive factor of response to anti-angiogenic therapies.

Furthermore, colorectal patients with higher plasma levels of PD-ECGF had a significantly higher risk of early progression, as represented by a significant hazard ratio analysis for PD-ECGF and tumor progression (Hazard ratio, $p<0.041$). Therefore, PD-ECGF plasma protein levels have a potential value in predicting cancer response to therapy as a predictive factor of response to anti-angiogenic therapies.

These findings support the use of PD-ECGF as a novel biomarker for detection, diagnosis, disease monitoring and prediction of response in patients with RCC, breast cancer, colorectal cancer and other type of cancers.

Thus, in a first aspect, the present invention relates to a method for the diagnosis of cancer in a subject that comprises
(i) determining the levels of PD-ECGF in a sample from said subject and,
(ii) comparing the levels obtained in (i) to a reference value, wherein
  if the levels of PD-ECGF in a sample from the subject are increased when compared to a reference value, then the subject is diagnosed with cancer, and
  if the levels of PD-ECGF in a sample from the subject are decreased when compared to a reference value, then the subject is not diagnosed with cancer.

In another aspect, the invention relates to a method for predicting the response of a subject suffering from cancer to an anti-angiogenic treatment, wherein said anti-angiogenic treatment is not doxorubicin or interferon therapy, that comprises
  (i) determining the levels of PD-ECGF in a sample from said subject and,
  (ii) comparing the levels obtained in (i) to a reference value,
  wherein
    if the levels of PD-ECGF in a sample from the subject are increased when compared to a reference value, it is indicative of a bad response to the anti-angiogenic treatment, and
    if the levels of PD-ECGF in a sample from the subject are decreased when compared to a reference value, it is indicative of a good response to the anti-angiogenic treatment.

In a further aspect, the invention relates to the use of PD-ECGF in the diagnosis of cancer in a subject and/or in the determination of the response of a cancer patient to an anti-angiogenic treatment, wherein said anti-angiogenic treatment is not doxorubicin or interferon therapy.

DETAILED DESCRIPTION OF THE INVENTION

Definitions

Figure 1:
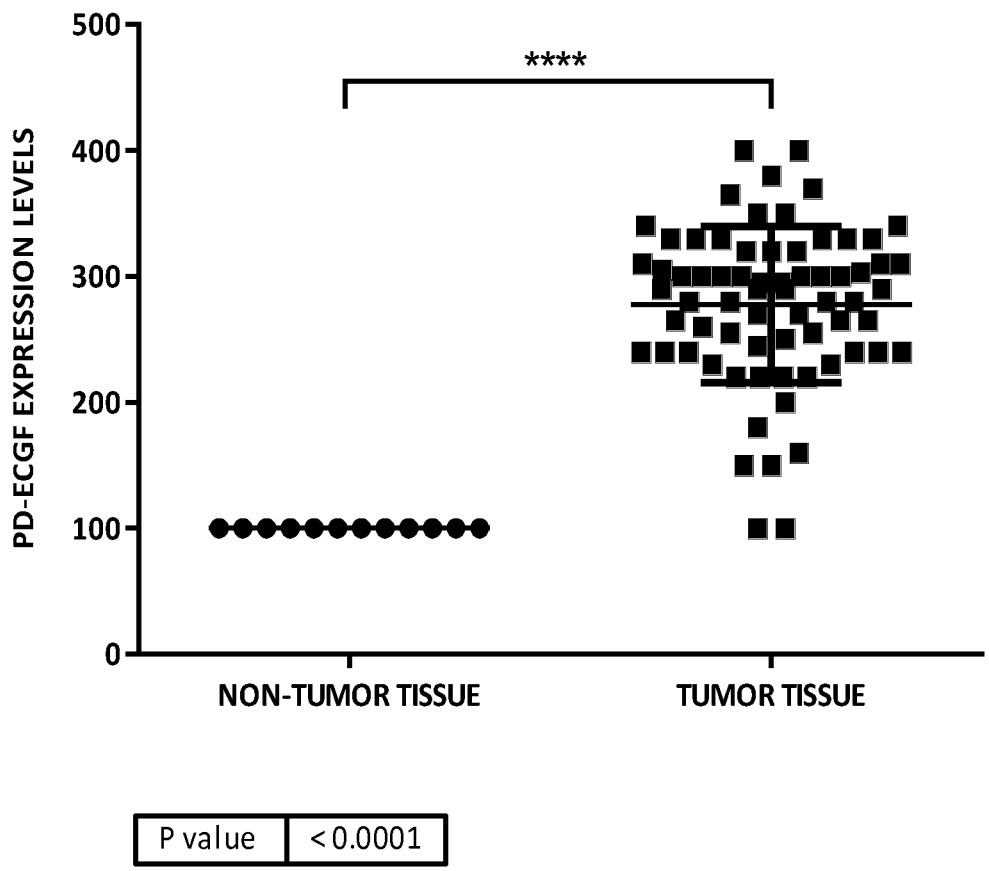
FIG. 1. Levels of PD-ECGF protein from tumor or non-tumor tissue samples of patients or healthy subjects measured by inmunohistochemistry.

The term "anti-angiogenic treatment" or "anti-angiogenesis treatment", as used herein, relates to a treatment based on at least one anti-angiogenesis agent. The term "anti-angiogenic agent" or "anti-angiogenesis agent" or "angiogenesis inhibitor", relates to an agent targeted to angiogenesis (e.g. the process of forming blood vessels) including, but not limited to, tumor angiogenesis. In this context, inhibition can refer to blocking the formation of blood vessels and halting or slowing down the growth of blood vessels.

The term "cancer" is referred to a disease characterized by uncontrolled cell division (or by an increase of survival or apoptosis resistance) and by the ability of said cells to invade other neighboring tissues (invasion) and spread to other areas of the body where the cells are not normally located (metastasis) through the lymphatic and blood vessels, circulate through the bloodstream, and then invade normal tissues elsewhere in the body. Depending on whether or not they can spread by invasion and metastasis, tumors are classified as being either benign or malignant: benign tumors are tumors that cannot spread by invasion or metastasis, i.e., they only grow locally; whereas malignant tumors are tumors that are capable of spreading by invasion and metastasis. Biological processes known to be related to cancer include angiogenesis, immune cell infiltration, cell migration and metastasis. The term cancer includes, without limitation, lung cancer, sarcoma, malignant melanoma, pleural mesothelioma, bladder carcinoma, prostate cancer, pancreas carcinoma, gastric carcinoma, ovarian cancer, hepatoma, breast cancer, colorectal cancer, kidney cancer, esophageal cancer, suprarenal cancer, parotid gland cancer, head and neck carcinoma, cervix cancer, endometrial cancer, liver cancer, mesothelioma, multiple myeloma, leukaemia, and lymphoma. In a particular embodiment of the invention, the cancer is renal cell carcinoma (RCC), breast cancer, or colorectal cancer. The term "breast cancer" relates to any malignant proliferative disorder of breast cells, most commonly from the inner lining of milk ducts or the lobules that supply the ducts with milk. Cancers originating from ducts are known as ductal carcinomas, while those originating from lobules are known as lobular carcinomas. The term "colorectal cancer" also known as "colon cancer", "rectal cancer", or "bowel cancer", refers to a cancer from uncontrolled cell growth in the colon or rectum, or in the appendix. The term "renal cell carcinoma" also known as "kidney cancer" or "renal adenocarcinoma" relates to cancer wherein tumor cells are found in any tissue of the kidney including clear cell carcinomas (mixed with granular cells or not), chromophilic cancers, rhabdoid tumors of the kidney, chromophobic cancers, oncocytic cancers, collecting duct cancers, transitional cell carcinomas and sarcomatoid tumors.

The term "diagnosis", as used herein, refers both to the process of attempting to determine and/or identify a possible disease in a subject, i.e. the diagnostic procedure, and to the opinion reached by this process, i.e. the diagnostic opinion. As such, it can also be regarded as an attempt at classification of an individual's condition into separate and distinct categories that allow medical decisions about treatment and prognosis to be made. In particular, the term "diagnosis of cancer" relates to the capacity to identify or detect the presence of a tumor in a subject. This detection, as it is understood by a person skilled in the art, does not claim to be correct in 100% of the analyzed samples. However, it requires that a statistically significant amount of the analyzed samples are classified correctly. The amount that is statistically significant can be established by a person skilled in the art by means of using different statistical tools; illustrative, non-limiting examples of said statistical tools include determining confidence intervals, determining the p-value, the Student's t-test or Fisher's discriminant functions, etc. (see, for example, Dowdy and Wearden, Statistics for Research, John Wiley & Sons, New York 1983). The confidence intervals are preferably at least 90%, at least 95%, at least 97%, at least 98% or at least 99%. The p-value is preferably less than 0.1, less than 0.05, less than 0.01, less than 0.005 or less than 0.0001. The teachings of the present invention preferably allow correctly diagnosing in at least 60%, in at least 70%, in at least 80%, or in at least 90% of the subjects of a determined group or population analyzed.

The term "expression level", as used herein, refers to the measurable quantity of gene product produced by the gene in a sample of the subject, wherein the gene product can be a transcriptional product or a translational product. As understood by the person skilled in the art, the gene expression level can be quantified by measuring the messenger RNA levels of said gene or of the protein encoded by said gene. In the context of the present invention, the expression level of the gene encoding PD-ECGF can be determined by measuring the levels of mRNA encoded by said gene, or by measuring the levels of the protein encoded by said gene, i.e. PD-ECGF protein or of variants thereof. PD-ECGF protein variants include all the physiologically relevant post-translational chemical modifications forms of the protein, for example, glycosylation, phosphorylation, acetylation, etc., provided that the functionality of the protein is maintained. Said term encompasses the PD-ECGF protein of any mammal species, including but not being limited to domestic and farm animals (cows, horses, pigs, sheep, goats, dogs, cats or rodents), primates and humans. Preferably, the PD-ECGF protein is a human protein.

The term "plateled derived-endothelial cell growth factor" or "PD-ECGF", as used herein, is also known as "plateled-derived endothelial cell growth factor-1", "ECGF-1" or "ECGF1", "gliostatin", "platelet-derived endothelial cell mitogen" "thymidine phosphorylase" or "TP", and relates to a cytoplasmic protein initially isolated from platelets showing endothelial mitogenic activity. It is an acidic non-glycosylated protein of 45 kDa, which is synthesized as a precursor of 482 amino acids from which it is derived by N-terminal processing. The protein isolated from placenta contains five additional amino acids at the N-terminus. PD-ECGF can be phosphorylated in vivo at serine residues but the biological significance of this phosphorylation step is unknown. The human gene encoding PD-ECGF is located on chromosome 22 and assigned Gene ID 1890 (NCBI GenBank, 1 Mar. 2014 update). A number of transcript variants have been described for PD-ECGF: transcript variant 1 (accession number NM_001113755.2 in NCBI GenBank), encoding the same isoform 1 than variants 2, 3 and 4; transcript variant 2 (NM_001953.4), which uses an alternate splice site in the 5' UTR; transcript variant 3 (NM_001113756.2), which differs in the 5' UTR compared to variant 1; transcript variant 4 (NM_001257988.1), which uses an alternate splice site in the 5' UTR compared to variant 1; and transcript variant 5 (NM_001257989.1), which uses alternate splice sites in the 5' UTR and the 3' coding region compared to variant 1, and coding for isoform 2, said isoform 2 having an additional segment in the C-terminal region compared to isoform 1. The amino acid sequence of human PD-ECGF is located in NCBI GenBank under accession number AAB03344.2 (482 amino acids, version as of 3 Feb. 2000) and under UniProtKB/Swiss-Prot accession number P19971.2 (Uniprot version 167 as of 19 Feb. 2014).

The term "predicting the response to an anti-angiogenic treatment", as used herein, relates to the prediction of a medical outcome following a therapeutic intervention using an anti-angiogenic treatment. The outcome after the treatment may be determined using any common end point for patient progression, such as, for example, a poor or good outcome (e.g., likelihood of long-term survival, overall survival, disease-specific survival, progression-free survival or disease-free survival); relapse, disease progression, or mortality. As will be understood by those skilled in the art, the prediction of the response, although preferred to be, need not be correct for 100% of the subjects to be diagnosed or evaluated. The term, however, requires that a statistically significant portion of subjects can be identified as having an increased probability of having a given outcome in response to the therapy. Whether a subject is statistically significant can be determined without further ado by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983. Preferred confidence intervals are at least 50%, at least 60%, at least 70%, at least 80%, at least 90% at least 95%. The p-values are, preferably 0.05, 0.025, 0.001 or lower. Any parameter which is widely accepted for determining response of a patient can be used in the present invention including, without limitation of disease progression.

The term "reference value", as used herein, refers to a laboratory value used as a reference for values/data obtained by laboratory examinations of subjects or samples collected from subjects. The reference value or reference level can be an absolute value, a relative value, a value that has an upper or a lower limit, a range of values, an average value, a median value, a mean value, or a value as compared to a particular control or baseline value. A reference value can be based on an individual sample value, such as for example, a value obtained from a sample from the subject being tested, but at an earlier point in time. The reference value can be based on a large number of samples, such as from population of subjects of the chronological age matched group, or based on a pool of samples including or excluding the sample to be tested. Suitable reference values are indicated in the context of the methods of the invention for determining cancer diagnosis or predicting the response of a subject with cancer that is being treated with anti-angiogenic therapies.

The term "sample" or "biological sample", as used herein, refers to biological material isolated from a subject. The biological sample contains any biological material suitable for detecting RNA or protein levels. In a particular embodiment, the sample comprises genetic material, e.g., DNA, genomic DNA (gDNA), complementary DNA (cDNA), RNA, heterogeneous nuclear RNA (hnRNA), mRNA, etc., from the subject under study. The sample can be isolated from any suitable tissue or biological fluid such as, for example blood, saliva, plasma, serum, urine, cerebrospinal liquid (CSF), feces, a surgical specimen, a specimen obtained from a biopsy, and a tissue sample embedded in paraffin. Methods for isolating samples are well known to those skilled in the art. In particular, methods for obtaining a sample from a biopsy include gross apportioning of a mass, or micro-dissection or other art-known cell-separation methods. In order to simplify conservation and handling of the samples, these can be formalin-fixed and paraffin-embedded or first frozen and then embedded in a cryosolidifiable medium, such as OCT-Compound, through immersion in a highly cryogenic medium that allows rapid freeze. In a particular embodiment, the sample from the subject according to the methods of the present invention is a biological fluid sample. In a particular embodiment, the sample from the subject according to the methods of the present invention is selected from the group consisting of blood, serum, plasma, and a tissue sample; more preferably from the group consisting of plasma and a tissue sample.

The term "subject" or "individual" or "animal" or "patient" or "mammal," relates to all the animals classified as mammals and includes but is not limited to domestic and farm animals, primates and humans, for example, human beings, non-human primates, cows, horses, pigs, sheep, goats, dogs, cats, or rodents. Preferably, the subject is a male or female human being of any age, sex or race.

The term "treatment", as used herein comprises any type of therapy, which aims at terminating, preventing, ameliorating and/or reducing the susceptibility to a clinical condition as described herein. In a preferred embodiment, the term treatment relates to prophylactic treatment (i.e. a therapy to reduce the susceptibility of a clinical condition, a disorder or condition as defined herein). Thus, "treatment," "treating," and the like, as used herein, refer to obtaining a desired pharmacologic and/or physiologic effect, covering any treatment of a pathological condition or disorder in a mammal, including a human. The effect may be prophylactic in terms of completely or partially preventing a disorder or symptom thereof and/or may be therapeutic in terms of a partial or complete cure for a disorder and/or adverse effect attributable to the disorder. That is, "treatment" includes (1) preventing the disorder from occurring or recurring in a subject, (2) inhibiting the disorder, such as arresting its development, (3) stopping or terminating the disorder or at least symptoms associated therewith, so that the host no longer suffers from the disorder or its symptoms, such as causing regression of the disorder or its symptoms, for example, by restoring or repairing a lost, missing or defective function, or stimulating an inefficient process, or (4) relieving, alleviating, or ameliorating the disorder, or symptoms associated therewith, where ameliorating is used in a broad sense to refer to at least a reduction in the magnitude of a parameter, such as inflammation, pain, and/or immune deficiency.

Cancer Diagnostic Method of the Invention

The authors of the present invention have found that PD-ECGF expression is not detected in non-cancerous tissue samples (0 in 12, 0%), while PD-ECGF protein expression is detected in 67 (>97%) tissue samples out of 69 RCC patients and in 9 (56%) out of 16 in tissue samples from breast cancer patients when tissue samples were analyzed by immunohistochemistry (see Example 1). Similarly, PD-ECGF expression was observed in 14 (>87%) plasma samples out of 16 RCC patients, in 11 (69%) out of 16 in plasma samples from breast cancer patients and in 52 (90%) out of 58 in plasma samples from colorectal cancer patients analyzed by ELISA (see Example 2).

Therefore, in a first aspect, the invention relates to a method for the diagnosis of cancer in a subject that comprises (i) determining the levels of PD-ECGF in a sample from said subject and, (ii) comparing the levels obtained in (i) to a reference value, wherein if the levels of PD-ECGF in a sample from the subject are increased when compared to a reference value, then the subject is diagnosed with cancer, and if the levels of PD-ECGF in a sample from the subject are decreased when compared to a reference value, then the subject is not diagnosed with cancer.

Thus, in a first step of the diagnostic method of the invention, the expression levels of PD-ECGF are determined in a sample from the subject whose diagnosis is to be determined. The sample wherein the expression level of PD-ECGF is determined can be any sample containing cells from the potential tumor. In a particular embodiment, the sample containing cells from the potential tumor is a biological fluid sample. In a particular embodiment, the sample containing cells from the potential tumor is potential tumor tissue or a portion thereof. In a more particular embodiment, said potential tumor tissue sample is a kidney tissue sample from a patient whose diagnosis of kidney cancer is to be determined, or a breast tissue sample from a patient whose diagnosis of breast cancer is to be determined, or a colorectal tissue sample from a patient whose diagnosis of colorectal cancer is to be determined. Said sample can be obtained by conventional methods, e.g., biopsy, surgical excision or aspiration, by using methods well known to those of ordinary skill in the related medical arts. Methods for obtaining the sample from the biopsy include gross apportioning of a mass, or microdissection or other art-known cell-separation methods including nephrectomy and partial tumorectomy. Tumor cells can additionally be obtained from fine needle aspiration cytology. In order to simplify conservation and handling of the samples, these can be formalin-fixed and paraffin-embedded or first frozen and then embedded in a cryosolidifiable medium, such as OCT-Compound, through immersion in a highly cryogenic medium that allows for rapid freeze.

In another embodiment, the sample wherein the expression level of PD-ECGF is determined is a biofluid from the patient whose diagnosis is to be determined. In a preferred embodiment, the biofluid is selected from blood, particularly peripheral blood, plasma or serum. The blood sample is typically extracted by means of puncturing an artery or vein, normally a vein from the inner part of the elbow or from the back of the hand, the blood sample being collected in an air-tight vial or syringe. A capillary puncture normally on the heel or on the distal phalanxes of fingers can be performed for analysis by means of a micromethod. Serum can be obtained from the complete blood sample and in the absence of anticoagulant by leaving the sample to settle for 10 minutes so that it coagulates and subsequently centrifuging it at 1,500 rpm for 10 minutes for the purpose of separating the cells (precipitate) from the serum (supernatant). In turn, to obtain the plasma sample the complete blood is contacted with an anticoagulant and is centrifuged at 3,000 rpm for 20 minutes. The precipitate of said centrifugation corresponds to the formed elements, and the supernatant corresponds to the plasma. The serum or the plasma obtained can be transferred to a storage tube for sample analysis by means of the method of the invention.

In a particular embodiment of the diagnostic method of the invention, the sample wherein PD-ECGF expression levels are determined is a plasma sample or a tissue sample. In a particular embodiment, PD-ECGF expression levels are determined in a plasma sample or in a breast tissue sample when diagnosis of breast cancer is to be determined. In a particular alternative embodiment, PD-ECGF expression levels are determined in a plasma sample or in a kidney tissue sample when diagnosis of renal cell carcinoma (RCC) is to be determined. In another particular alternative embodiment, PD-ECGF expression levels are determined in a plasma sample or in a colorectal tissue sample when diagnosis of colorectal cancer is to be determined.

As previously described, gene expression levels can be quantified by measuring the messenger RNA levels of the gene or of the protein encoded by said gene or of the protein encoded by said gene, i.e. PD-ECGF protein or of variants thereof. PD-ECGF protein variants include all the physiologically relevant post-translational chemical modifications forms of the protein, for example, glycosylation, phosphorylation, acetylation, etc., provided that the functionality of the protein is maintained. Said term encompasses the PD-ECGF protein of any mammal species, including but not being limited to domestic and farm animals (cows, horses, pigs, sheep, goats, dogs, cats or rodents), primates and humans. Preferably, the PD-ECGF protein is a human protein.

In order to measure the mRNA levels of a gene, the biological sample may be treated to physically, mechanically or chemically disrupt tissue or cell structure, to release intracellular components into an aqueous or organic solution to prepare nucleic acids for further analysis. The nucleic acids are extracted from the sample by procedures known to the skilled person and commercially available. RNA is then extracted from frozen or fresh samples by any of the methods typical in the art, for example, Sambrook, J., et al., 2001. Molecular cloning: A Laboratory Manual, $3^{rd}$ ed., Cold Spring Harbor Laboratory Press, N.Y., Vol. 1-3. Preferably, care is taken to avoid degradation of the RNA during the extraction process.

The expression level can be determined using mRNA obtained from a formalin-fixed, paraffin-embedded tissue sample. mRNA may be isolated from an archival pathological sample or biopsy sample which is first deparaffinized. An exemplary deparaffinization method involves washing the paraffinized sample with an organic solvent, such as xylene. Deparaffinized samples can be rehydrated with an aqueous solution of a lower alcohol. Suitable lower alcohols, for example, include methanol, ethanol, propanols and butanols. Deparaffinized samples may be rehydrated with successive washes with lower alcoholic solutions of decreasing concentration, for example. Alternatively, the sample is simultaneously deparaffinized and rehydrated. The sample is then lysed and RNA is extracted from the sample. Samples can be also obtained from fresh tumor tissue such as a resected tumor. In a particular embodiment samples can be obtained from fresh tumor tissue or from OCT embedded frozen tissue. In another preferred embodiment samples can be obtained by colonoscopy and then paraffin-embedded.

In order to normalize the values of mRNA expression among the different samples, it is possible to compare the expression levels of the mRNA of interest in the test samples with the expression of a control RNA. A "control RNA" as used herein, relates to RNA whose expression levels do not change or change only in limited amounts in tumor cells with respect to non-tumorigenic cells. Preferably, the control RNA is mRNA derived from housekeeping genes and which code for proteins which are constitutively expressed and carry out essential cellular functions. Preferred housekeeping genes for use in the present invention include β-2-microglobulin, ubiquitin, 18-S ribosomal protein, cyclophilin, IPO8, HPRT, GAPDH, PSMB4, tubulin and β-actin. In a preferred embodiment, the control RNA is GAPDH, IPO8, HPRT, β-actin, 18-S ribosomal protein or PSMB4 mRNA.

In one embodiment relative gene expression quantification is calculated according to the comparative threshold cycle (Ct) method using GAPDH, IPO8, HPRT, β-actin or PSMB4 as an endogenous control and commercial RNA controls as calibrators. Final results are determined according to the formula 2-(ΔCt sample-ΔCt calibrator), where ΔCT values of the calibrator and sample are determined by subtracting the Ct value of the target gene from the value of the control gene.

Suitable methods to determine gene expression levels at the mRNA level include, without limitation, standard assays for determining mRNA expression levels such as qPCR, RT-PCR, RNA protection analysis, Northern blot, RNA dot blot, in situ hybridization, microarray technology, tag based methods such as serial analysis of gene expression (SAGE) including variants such as LongSAGE and SuperSAGE, microarrays, fluorescence in situ hybridization (FISH), including variants such as Flow-FISH, qFiSH and double fusion FISH (D-FISH), and the like.

Suitable methods to determine gene expression levels at the protein level include, without limitation, conventional methods for determining protein expression levels, such as using antibodies with a capacity to specifically bind to the proteins encoded by said genes (or to fragments thereof containing antigenic determinants) and subsequent quantification of the resulting antibody-antigen complexes. In a particular embodiment, PD-ECGF protein levels can be quantified by using standard assays for determining protein expression levels such as Western-blot or Western transfer, ELISA (enzyme-linked immunosorbent assay), RIA (radioimmunoassay), competitive EIA (competitive enzyme immunoassay), DAS-ELISA (double antibody sandwich ELISA), immunocytochemical and immunohistochemical techniques, techniques based on the use of protein biochips or microarrays which include specific antibodies or assays based on colloidal precipitation in formats such as dipsticks.

The antibodies to be employed in these assays can be, for example, polyclonal sera, hybridoma supernatants or monoclonal antibodies, antibody fragments, Fv, Fab, Fab' and F(ab')2, ScFv, diabodies, triabodies, tetrabodies and humanized antibodies. At the same time, the antibodies can be labeled or not. Illustrative, but non-exclusive examples of markers which can be used include radioactive isotopes, enzymes, fluorophores, chemiluminescent reagents, enzymatic substrates or cofactors, enzymatic inhibitors, particles, colorants, etc. There are a wide variety of well-known assays that can be used in the present invention, which use non-labeled antibodies (primary antibody) and labeled antibodies (secondary antibodies); among these techniques are included Western blot or Western transfer, ELISA, RIA, competitive EIA, DAS-ELISA, immunocytochemical and immunohistochemical techniques, techniques based on the use of biochips or protein microarrays including specific antibodies or assays based on colloidal precipitation in formats such as dipsticks. Other ways of detecting and quantifying the levels of the protein of interest include techniques of affinity chromatography, binding-ligand assays, etc.

On the other hand, the determination of the levels of the PD-ECGF protein can be carried out by constructing a tissue microarray (TMA) containing the subject samples assembled, and determining the expression levels of the corresponding protein by immunohistochemistry techniques. Immunostaining intensity can be evaluated by two or more different pathologists and scored using uniform and clear cut-off criteria, in order to maintain the reproducibility of the method. Discrepancies can be resolved by simultaneous re-evaluation. Briefly, the result of immunostaining can be recorded as negative expression (0) versus positive expression, and low expression (1+) versus moderate (2+) and high (3+) expression, taking into account the expression in tumor cells and the specific cut-off for each marker. As a general criterion, the cut-offs are selected in order to facilitate reproducibility, and when possible, to translate biological events. Alternatively, the immunostaining intensity can be evaluated by using imaging techniques and automated methods such as those disclosed in Rojo, M. G. et al. (Folia Histochem. Cytobiol. 2009; 47: 349-54) or Mulrane, L. et al. (Expert Rev. Mol. Diagn. 2008; 8: 707-25).

Alternatively, in another particular embodiment, the levels of the PD-ECGF protein are determined by Western blot. Western blot is based on the detection of proteins previously resolved by gel electrophoreses under denaturing conditions and immobilized on a membrane, generally nitrocellulose, by the incubation with an antibody specific and a developing system (e.g. chemoluminiscent).

In a particular embodiment, PD-ECGF expression levels to be determined in the diagnostic method of the invention are determined as PD-ECGF protein levels. In a more particular embodiment, PD-ECGF protein levels are determined by ELISA, western blot or by immunohistochemistry.

The term "activity level" of a protein, more particularly of an enzyme, as used herein refers to a measure of the enzyme activity, particularly measured as moles of substrate converted per unit of time.

Assays to determine the activity level of an enzyme are known by the skilled person and include, without limitation, initial rate assays, progress curve assays, transient kinetics assays and relaxation assays. Continuous assays of enzymatic activity include, without limitation, spectrophotometric, fluorometric, calorimetric, chemiluminiscent, light scattering and microscale thermopheresis assays. Discontinuous assays of enzymatic activity include, without limitation, radiometric and chromatographic assays. As the skilled person understands, factors that may influence enzymatic activity comprise salt concentration, temperature, pH, and substrate concentration.

In a second step of the diagnostic method of the invention, the expression levels of PD-ECGF in the sample from a subject whose diagnosis is to be determined are compared to a reference value.

In the context of the method of the invention for the diagnosis of cancer in a subject, the reference value is the PD-ECGF expression level determined in a sample from a healthy subject, i.e. a subject not diagnosed with cancer, or in a non-tumor tissue sample from a subject diagnosed with cancer, preferably the reference value is the PD-ECGF expression level determined a sample from a healthy subject, or in a subject not diagnosed with cancer.

Once this reference value is established, the level of PD-ECGF expressed in the sample can be compared with said reference value, and thus be assigned a level of "increased" or "decreased" expression. For example, an increase in expression levels above the reference value of at least 1.1-fold, 1.5-fold, 5-fold, 10-fold, 20-fold, 30-fold, 40-fold, 50-fold, 60-fold, 70-fold, 80-fold, 90-fold, 100-fold or even more compared with the reference value is considered as "increased" expression level. On the other hand, a decrease in expression levels below the reference value of at least 0.9-fold, 0.75-fold, 0.2-fold, 0.1-fold, 0.05-fold, 0.025-fold, 0.02-fold, 0.01-fold, 0.005-fold or even less compared with reference value is considered as "decreased" expression level.

Thus, if an increased expression level of PD-ECGF in the sample from a subject whose diagnosis is to be determined when compared to a reference value is observed, then the subject is diagnosed with cancer. Alternatively, if a decreased expression level of PD-ECGF in the sample from a subject whose diagnosis is to be determined when compared to the reference value, then the subject is not diagnosed with cancer.

Method for Predicting the Response to an Anti-Angiogenic Treatment According to the Invention The authors of the present invention have found that the levels of PD-ECGF determined in cancer patients show a statistically significant correlation with the risk that the patients shows early progression after treatment with an anti-angiogenic therapy. Thus, in a further aspect, the invention relates to a method for predicting the response to treatment in a subject suffering from cancer and undergoing an anti-tumoral treatment that comprises (i) determining the levels of PD-ECGF in a sample from said subject and,
(ii) comparing the levels obtained in (i) to a reference value, wherein if the levels of PD-ECGF in a sample from the subject are increased when compared to a reference value, it is indicative of a poor response of the cancer patient to the treatment, and if the levels of PD-ECGF in a sample from the subject are decreased when compared to a reference value, it is indicative of a good response of the cancer patient to the treatment.

In a particular embodiment, the invention relates to a method for predicting the response of a subject suffering from cancer to an anti-angiogenic treatment that comprises (i) determining the levels of PD-ECGF in a sample from said subject and,
(ii) comparing the levels obtained in (i) to a reference value, wherein if the levels of PD-ECGF in a sample from the subject are increased when compared to a reference value, it is indicative of a bad response to the anti-angiogenic treatment, and if the levels of PD-ECGF in a sample from the subject are decreased when compared to a reference value, it is indicative of a good response to the anti-angiogenic treatment.

In a more particular embodiment, the invention relates to a method for predicting the response of a subject suffering from cancer to an anti-angiogenic treatment, wherein said anti-angiogenic treatment is not doxorubicin or interferon therapy, that comprises (i) determining the levels of PD-ECGF in a sample from said subject and,
(ii) comparing the levels obtained in (i) to a reference value, wherein if the levels of PD-ECGF in a sample from the subject are increased when compared to a reference value, it is indicative of a bad response to the anti-angiogenic treatment, and if the levels of PD-ECGF in a sample from the subject are decreased when compared to a reference value, it is indicative of a good response to the anti-angiogenic treatment.

In a first step of the method of the invention for predicting the response to an anti-angiogenic treatment, the expression levels of PD-ECGF are determined in a sample from a subject suffering from cancer whose response to treatment is to be predicted.

The sample wherein the expression level of PD-ECGF is determined can be any sample containing cells from the tumor. In a particular embodiment, the sample containing cells from the potential tumor is a biological fluid sample. In a particular embodiment, the sample containing cells from the tumor is tumor tissue or a portion thereof. In a more particular embodiment, said tumor tissue sample is a kidney tumor tissue sample from a patient whose response to anti-angiogenic treatment of kidney cancer is to be predicted, or a breast tumor tissue sample from a patient whose response to anti-angiogenic treatment of breast cancer is to be predicted, or a colorectal tumor tissue sample from a patient whose response to anti-angiogenic treatment of colorectal cancer is to be predicted. Said sample can be obtained by conventional methods, e.g., biopsy, surgical excision or aspiration, by using methods well known to those of ordinary skill in the related medical arts and previously described in the context of the diagnostic method of the invention. In one embodiment, the sample containing tumor cells is a sample of the primary tumor. In another embodiment, the tumor is a metastatic tumor and the sample wherein the PD-ECGF levels are determined is a sample from the metastasis.

In another embodiment, the sample wherein the expression level of PD-ECGF is determined is a biofluid from the patient suffering from cancer whose response to treatment is to be predicted. In a preferred embodiment, the biofluid is selected from blood, particularly peripheral blood, plasma or serum. Methods for the obtention of blood, serum, and plasma samples are known by the skilled person and have been described previously in the context of the diagnostic method of the invention.

In a particular embodiment method of the invention for predicting the response to an anti-angiogenic treatment, the sample wherein PD-ECGF expression levels are determined is a plasma sample or a tissue sample. In a particular embodiment, PD-ECGF expression levels are determined in a plasma sample or in a breast tumor tissue sample when response to anti-angiogenic treatment of breast cancer is to be predicted. In a particular alternative embodiment, PD-ECGF expression levels are determined in a plasma sample or in a kidney tumor tissue sample when response to anti-angiogenic treatment of renal cell carcinoma (RCC) is to be predicted. In another particular alternative embodiment, PD-ECFG expression levels are determined in a plasma sample or in a colorectal tumor tissue sample when response to anti-angiogenic treatment of colorectal cancer is to be predicted.

As previously described, gene expression levels can be quantified by measuring the messenger RNA levels of the gene or of the protein encoded by said gene or of the protein encoded by said gene, i.e. PD-ECGF protein or of variants thereof. PD-ECGF protein variants have been described above and are incorporated herein.

Methods to determine expression levels based on mRNA levels and protein levels, particularly PD-ECGF mRNA levels and PD-ECGF protein levels, have been described previously in the context of the diagnostic method of the invention and incorporated herein.

In a particular embodiment, PD-ECGF expression levels to be determined in the prediction of response to anti-angiogenic treatment method of the invention are determined as PD-ECGF protein levels. In a more particular embodiment, PD-ECGF protein levels are determined by ELISA, western blot or by immunohistochemistry.

In a particular embodiment, the subject suffering from cancer whose prediction of response to treatment is to be determined by the method of the invention is undergoing an anti-angiogenic treatment, wherein said anti-angiogenic treatment of cancer is based on at least one anti-angiogenesis agent.

Anti-angiogenic agents and treatments according to the invention include, without limitation anti-VEGF agents, including monoclonal antibodies such as bevacizumab (Avastin, a recombinant humanized monoclonal IgG1 antibody that binds to and inhibits the biological activity of human VEGFA in in vitro and in vivo assay systems), antibody derivatives such as ranibizumab (Lucentis), or antibody fragments such as Fab IMC 1121 or F200 Fab or orally-available small molecules that inhibit the tyrosine kinases stimulated by VEGF such as lapatinib (Tykerb), sunitinib (Sutent), sorafenib (Nexavar), axitinib, and pazopanib; anti-fibroblast growth factor (anti-FGF) agents, such as suramin and its derivatives, pentosanpolysulfate, cediranib, pazopanib, or BIBF 1120); anti-EGF agents, such as cetuximab, gefitinib or erlotinib and anti-HGF agents, such as ARQ197, JNJ-38877605, PF-04217903, SGX523, NK4, or AMG102; and anti-angiogenic polypeptides such as angiostatin, endostatin, anti-angiogenic anti-thrombin III or sFRP-4.

Further anti-angiogenic agents include Marimastat; AG3340; COL-3, BMS-275291, Thalidomide, Endostatin, SU5416, SU6668, EMD121974, 2-methoxyoestradiol, carboxiamidotriazole, CMIOI (GBS toxin), pentosanpolysulphate, angiopoietin 2 (Regeneron), herbimycin A, PNU145156E, 16K prolactin fragment, Linomide, thalidomide, pentoxifylline, genistein, TNP470, endostatin, paclitaxel, accutin, angiostatin, cidofovir, vincristine, bleomycin, AGM-1470, platelet factor 4 or minocycline.

Further anti-angiogenic agents include anti-angiogenic polypeptides, denoting polypeptides capable of inhibiting angiogenesis and including, without limitation, angiostatin, endostatin, anti-angiogenic anti-thrombin III, sFRP-4 as described in WO2007115376, an anti-VEGF antibody such as anibizumab, bevacizumab (avastin), Fab IMC 1121 and F200 Fab.

Further anti-angiogenic agents include pegaptanib, sunitinib, pazopanib, sorafenib, vatalanib and aflibercept (VEGF-Trap).

Further anti-angiogenic agents include VEGFR2 blocking antibodies, such as Ramucirumab (IMC-1121B) and DC101 (also known as anti-Flk-1 mAb).

In a particular embodiment, the anti-angiogenic agent is selected from the group comprising sunitinib, bevacizumab, and DC101.

In one embodiment, the anti-angiogenic treatment is not a treatment comprising an anthracyclin antibiotic. In another embodiment, the anti-angiogenic treatment is not a treatment comprising doxorubicin. In another embodiment, the anti-angiogenic treatment is not a treatment comprising an interferon. In another embodiment, the anti-angiogenic treatment is not a treatment comprising a type I interferon and/or a type II interferon. In another embodiment, the anti-angiogenic treatment is not a treatment comprising IFN-α, IFN-β, IFN-ε, IFN-κ and IFN-ω. In another embodiment, the anti-angiogenic treatment is not a treatment comprising IFN-γ. In another embodiment, the anti-angiogenic treatment is an adjuvant treatment, i.e. after the surgical excision of the tumor. In one embodiment, the anti-angiogenic treatment is not an adjuvant treatment comprising interferon. In another embodiment, the anti-angiogenic treatment is not an adjuvant treatment comprising a type I interferon and/or a type II interferon. In another embodiment, the anti-angiogenic treatment is not an adjuvant treatment comprising IFN-α, IFN-β, IFN-ε, IFN-κ and IFN-ω. In another embodiment, the anti-angiogenic treatment is not an adjuvant treatment comprising IFN-γ.

Assays to determine the anti-angiogenic activity of a particular agent are described, without limitation, in WO 2003086299.

In a second step of the prediction of response method of the invention, the expression levels of PD-ECGF in the sample from a subject suffering from cancer whose prediction to anti-angiogenic treatment is to be determined are compared to a reference value.

In the context of the method of the invention for the prediction of response of cancer in a subject to the treatment with anti-angiogenic therapy, a suitable reference value can be the PD-ECGF expression level determined in a sample from a subject having cancer or having had cancer which has shown a good response to treatment with anti-angiogenic therapy, said expression levels having been determined at the time that the patient was being treated. In another embodiment, the reference value is the PD-ECGF levels in a healthy patient, i.e, a patient which has not been diagnosed with the type of cancer for which a prediction of the response to therapy is desired.

Once this reference value is established, the level of PD-ECGF expressed in the sample can be compared with said reference value, and thus be assigned a level of "increased" or "decreased" expression. For example, an increase in expression levels above the reference value of at least 1.1-fold, 1.5-fold, 5-fold, 10-fold, 20-fold, 30-fold, 40-fold, 50-fold, 60-fold, 70-fold, 80-fold, 90-fold, 100-fold or even more compared with the reference value is considered as "increased" expression level. On the other hand, a decrease in expression levels below the reference value of at least 0.9-fold, 0.75-fold, 0.2-fold, 0.1-fold, 0.05-fold, 0.025-fold, 0.02-fold, 0.01-fold, 0.005-fold or even less compared with reference value is considered as "decreased" expression level.

Thus, if an increased expression level of PD-ECGF in the sample from a subject suffering from cancer whose prediction of response to treatment is to be determined when compared to a reference value is observed, it is indicative of a poor response to treatment. Alternatively, if a decreased expression level of PD-ECGF in the sample from a subject suffering from cancer whose prediction of response to treatment is to be determined when compared to the reference value, it is indicative of a good response to treatment.

Uses of the Invention

In another aspect, the invention relates to the use of PD-ECGF in the diagnosis of cancer in a subject and/or in the prediction of the response of a cancer patient to an anti-angiogenic treatment. More in particular, the invention relates to the use of PD-ECGF in the diagnosis of cancer in a subject and/or in the prediction of the response of a cancer patient to an anti-angiogenic treatment, wherein said anti-angiogenic treatment is not doxorubicin or interferon therapy.

The terms "diagnosis of cancer" and "prediction of the response of a cancer patient to an anti-angiogenic treatment" have been defined above and are equally applicable to the uses according to the present invention. In a preferred embodiment, the cancer is selected from the group consisting of renal cell carcinoma (RCC), breast cancer and colorectal cancer. In a preferred embodiment, the use according to the invention comprises the use of the PD-ECGF polypeptide. In one embodiment, PD-ECGF polypeptide is used by determining the levels using a reagent which is capable of specifically binding to PD-ECGF, such as an antibody or an aptamer. In a preferred embodiment, the use according to the invention comprises the use of the polynucleotide encoding the PD-ECGF polypeptide. In one embodiment, the polynucleotide encoding the PD-ECGF polypeptide is used by determining the levels using a reagent which is capable of specifically binding to the polynucleotide encoding the PD-ECGF, such as a specific primer set or a probe.

The invention is described below by the following examples, which must be considered as merely illustrative and in no case limiting of the scope of the present invention.

EXAMPLES

Example 1. Identification of Tissue PD-ECGF Levels as a Cancer Marker for Detection, Diagnosis and Monitoring of Cancer in Patients. Determination of PD-ECGF Protein Levels in Non-Cancerous or Tumor Tissue Samples by Inmunohistochemistry PD-ECGF expression was analyzed in tumors from patients by immunodetection. A mouse monoclonal anti-thymidime phosphorylase [P-GF, 44C] antibody was used (Abeam, ab 3151).

Figure 2:
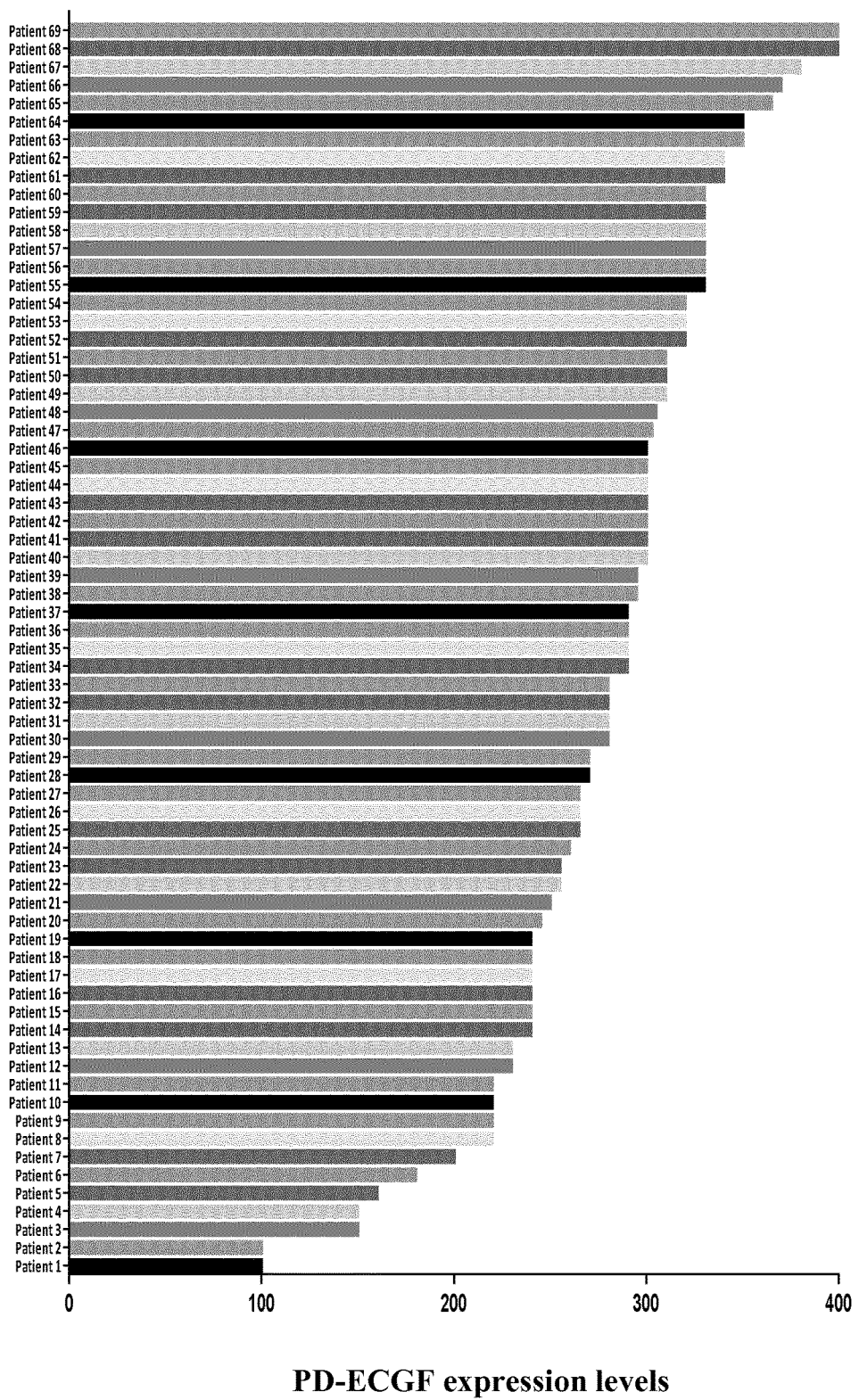
FIG. 2. Levels of PD-ECGF protein from tumor tissue samples of RCC Cancer patients measured by inmunohistochemistry.
Figure 3:
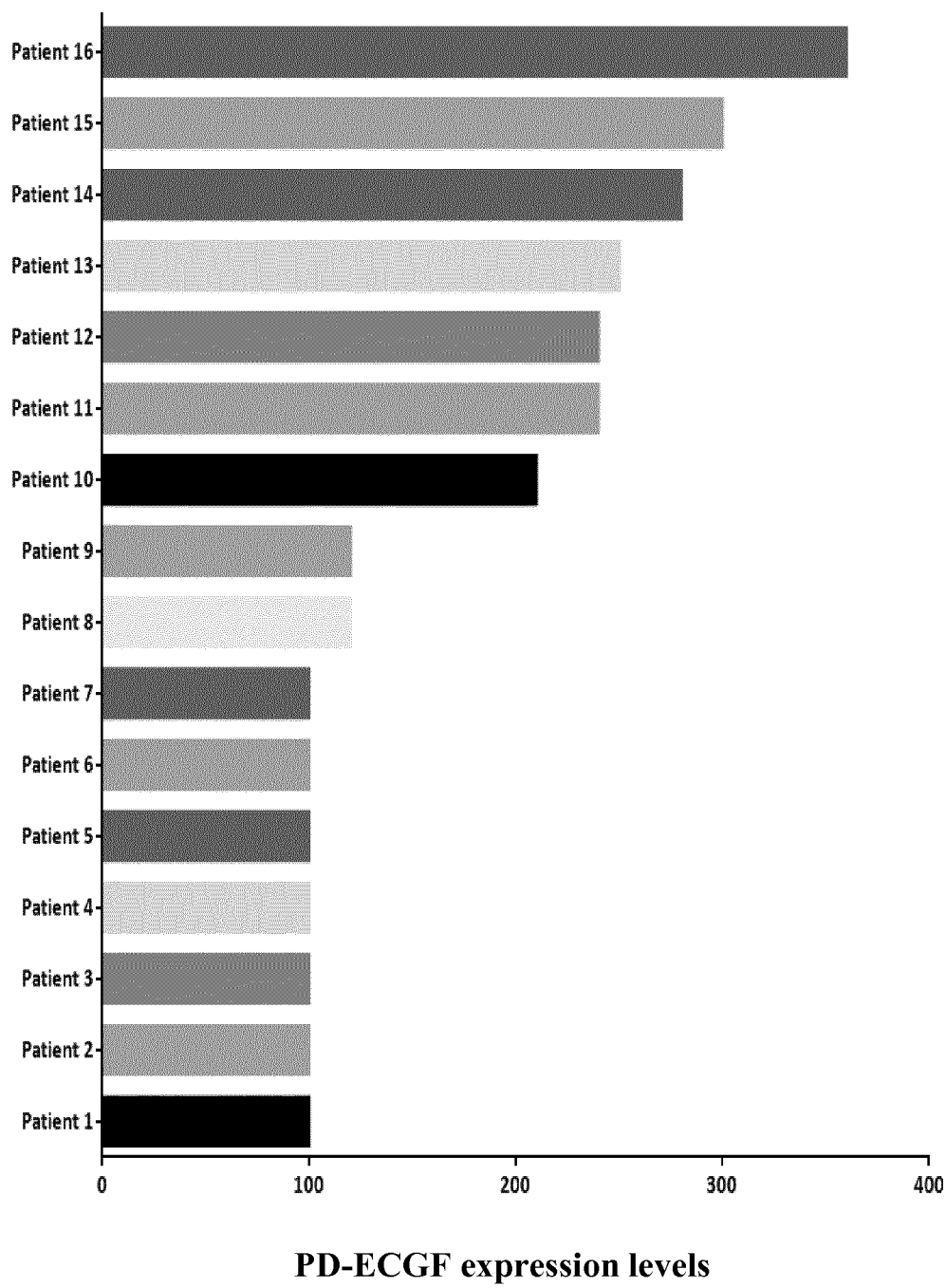
FIG. 3. Levels of PD-ECGF protein from tumor tissue samples of Breast Cancer patients measured by inmunohistochemistry.

Results showed that:
In 12 non-cancerous tissues, PD-ECGF was not detected; therefore there is a significant difference between the PD-ECGF levels of non-cancerous tissue and tumor mass in cancer patients (Mann-Whitney test, p<0.0001) (FIG. 1).
Protein expression of PD-ECGF was observed in 67 (>97%) tissue samples out of 69 RCC patients and in 9 (56%) out of 16 in tissues samples from breast cancer patients analyzed by inmunohistochemistry.
PD-ECGF has different locations (membrane, cytoplasm and nucleus), which allows evaluating the different degrees of expression according to location, and
PD-ECGF shows different expression levels depending on the intrinsic characteristics of each tumor.
When PD-ECGF basal (pre-treatment) expression levels were analyzed, it was observed that the tumors showed different basal expression levels (FIGS. 2 and 3), probably depending on the intrinsic characteristics of each tumor.

Example 2. Identification of Plasma PD-ECGF Levels as a Cancer Marker for Detection, Diagnosis and Monitoring of Cancer in Patients. Determination of PD-ECGF Protein Levels in Plasma Samples by ELISA PD-ECGF expression was analyzed in plasma from healthy subjects and cancer patients by ELISA. A human thymidine phosphorylase, TP ELISA Kit [CSB-E10814h] was used.

Figure 5:
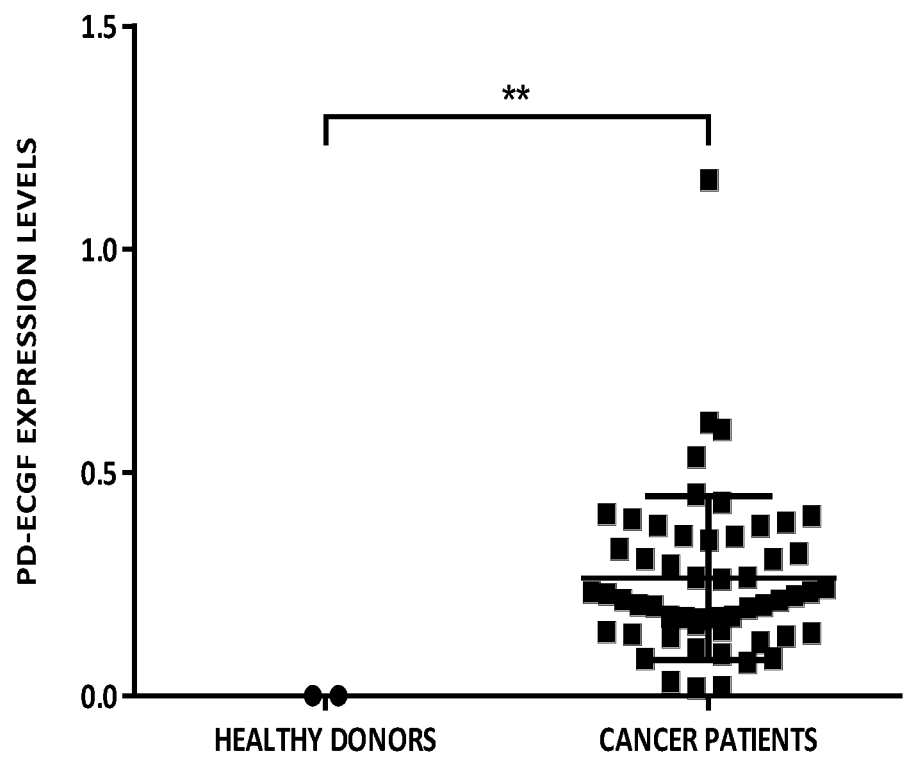
FIG. 5. PD-ECGF protein levels measured by ELISA from plasma samples of healthy donors or cancer patients.
Figure 6:
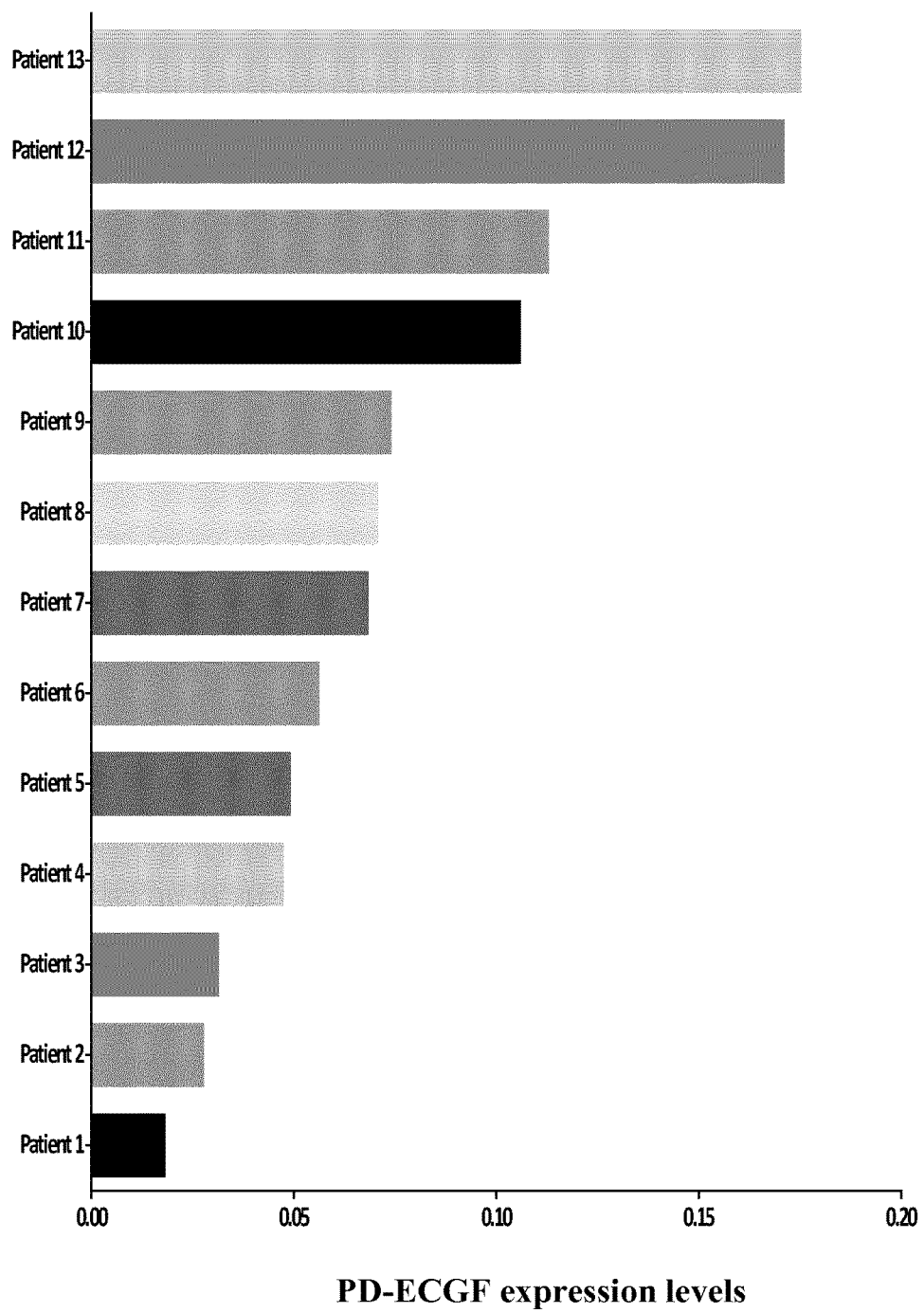
FIG. 6. PD-ECGF protein levels measured by ELISA from plasma samples of RCC cancer patients.
Figure 7:
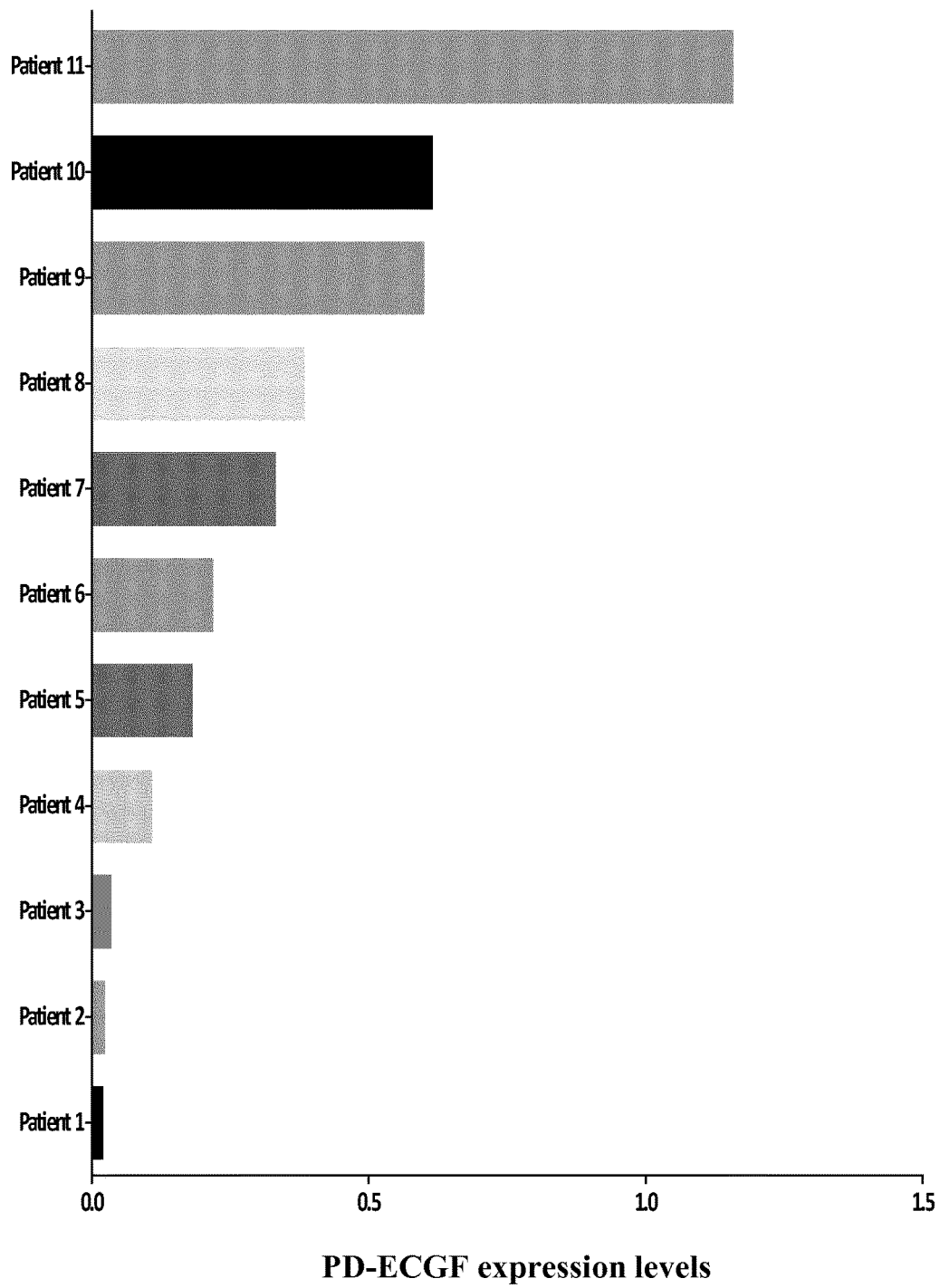
FIG. 7. PD-ECGF protein levels measured by ELISA from plasma samples of Breast Cancer patients.
Figure 8:
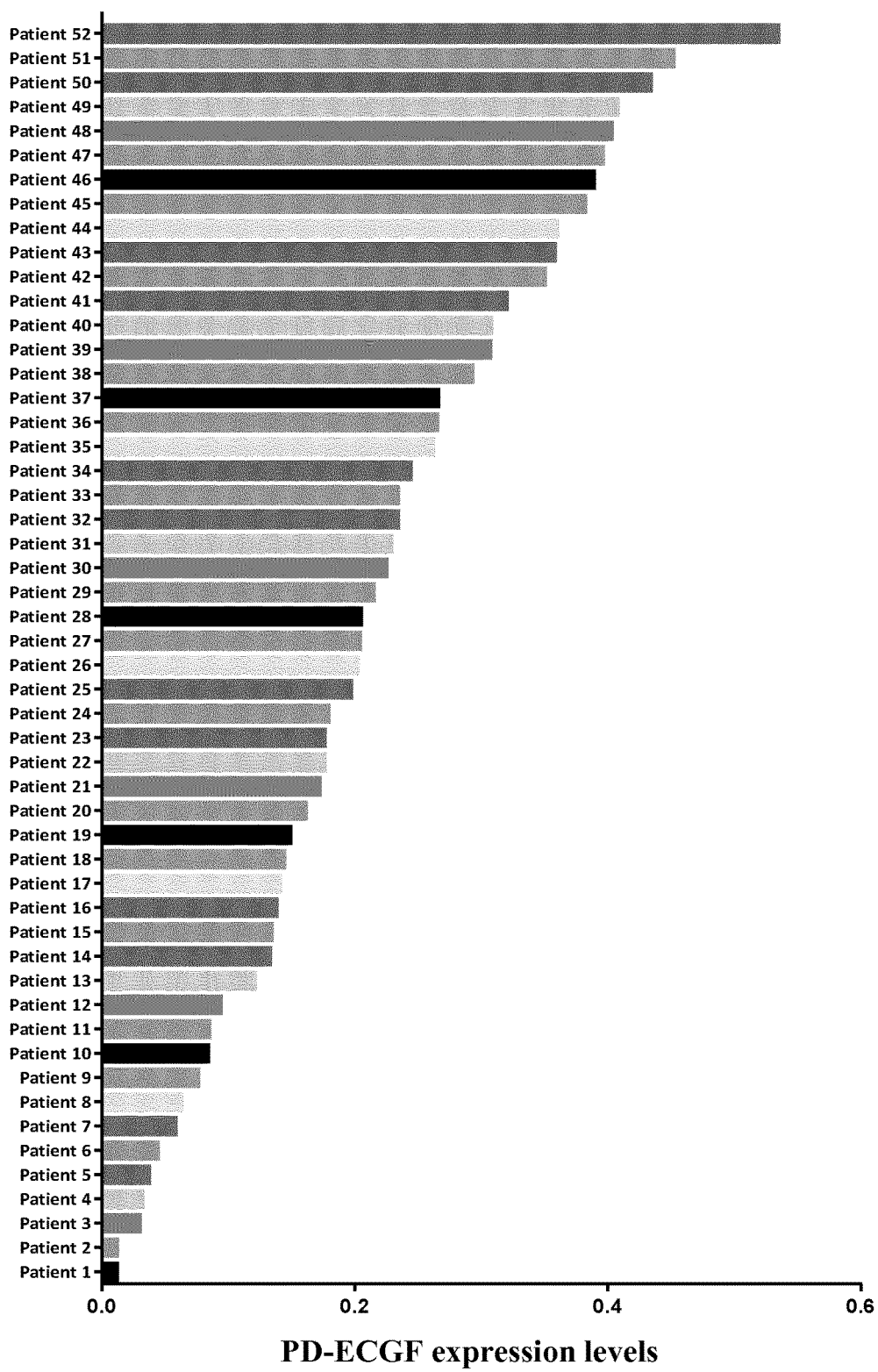
FIG. 8. PD-ECGF protein levels measured by ELISA from plasma samples of colorectal cancer patients.

Results showed that:
Plasma PD-ECGF levels were not detectable in healthy subjects compared to cancer patients. Quantitatively, there is a statistically significant difference between the PD-ECGF levels of healthy subjects and plasma levels of PD-ECGF in cancer patients (Mann-Whitney test, p=0.0013) (FIG. 5).
Protein expression of PD-ECGF was observed in 14 (>87%) plasma samples out of 16 RCC patients, in 11 (69%) out of 16 in plasma samples from breast cancer patients and in 52 (90%) out of 58 in plasma samples from colorectal cancer patients analyzed by ELISA.
PD-ECGF shows different expression levels depending on the characteristics of each patient.
When PD-ECGF basal expression levels were analyzed, it was observed that the patients showed different basal expression levels (FIGS. 6, 7 and 8), probably depending on the intrinsic characteristics of each patient.

Example 3. Identification of PD-ECGF as a Predictive Factor of Response to Anti-Angiogenic Treatment by Immunohistochemistry and ELISA PD-ECGF expression was analyzed in tumors from patients by immunodetection. A mouse monoclonal anti-thymidime phosphorylase [P-GF, 44C] antibody was used (Abcam, ab 3151).

Figure 4:
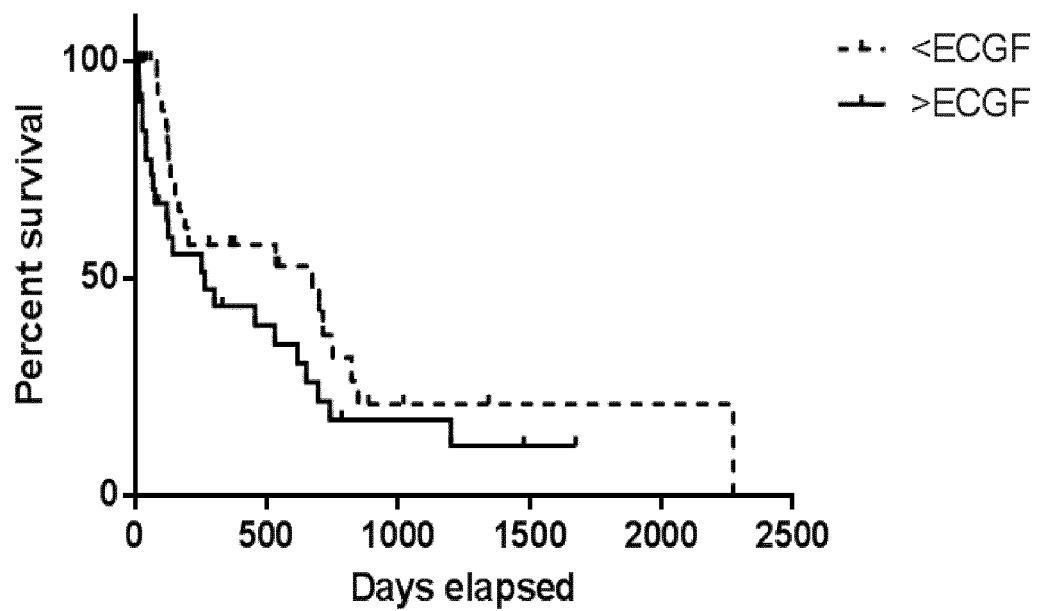
FIG. 4. Kaplan-Meier survival plot of progression free survival in RCC patients related with the tumor tissue levels of PD-ECGF expression.

Results showed that:
PD-ECGF was evaluated in RCC tissue samples from 63 patients; there is a significant association between higher tissue levels of PD-ECGF and higher risk of early progression in RCC patients (Kaplan-Meier and Gehan-Breslow-Wilcoxon test, p=0.045) (FIG. 4).
On the other hand PD-ECGF expression was analyzed in plasma from patients by ELISA. A human thymidine phosphorylase, TP ELISA Kit [CSB-E10814h] was used.

Figure 9:
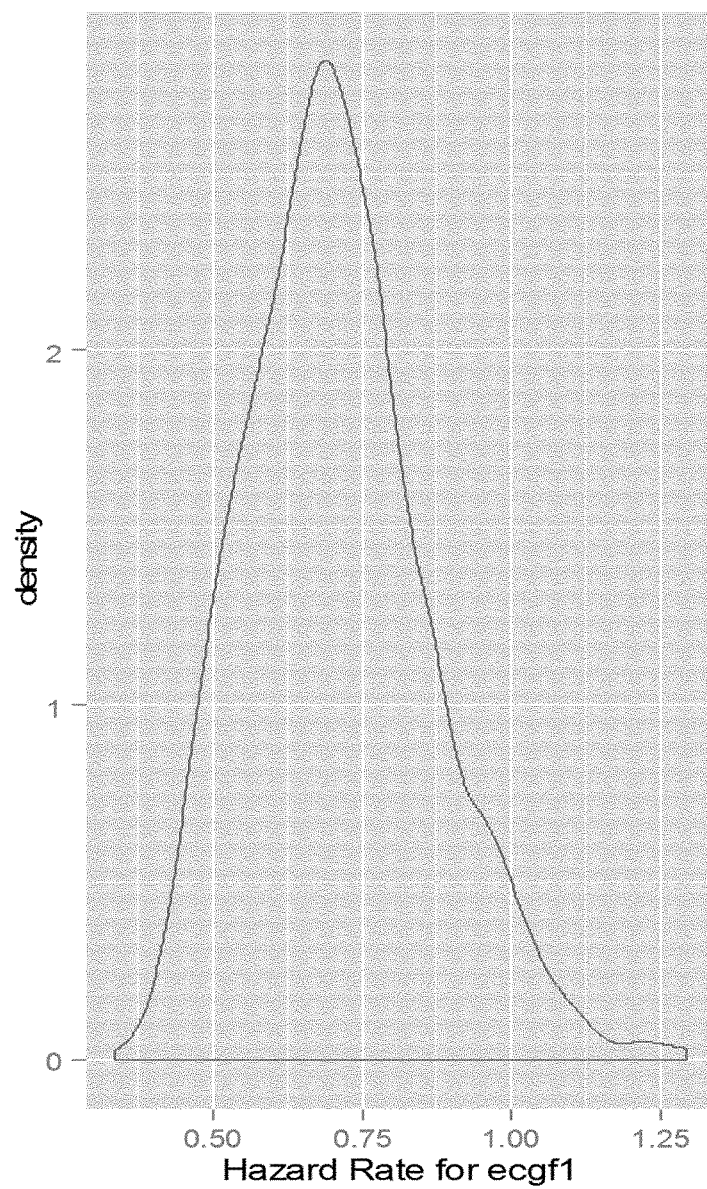
FIG. 9. Hazard Ratio association of PD-ECGF plasma protein levels to tumor progression in colorectal cancer patients.
Figure 10:
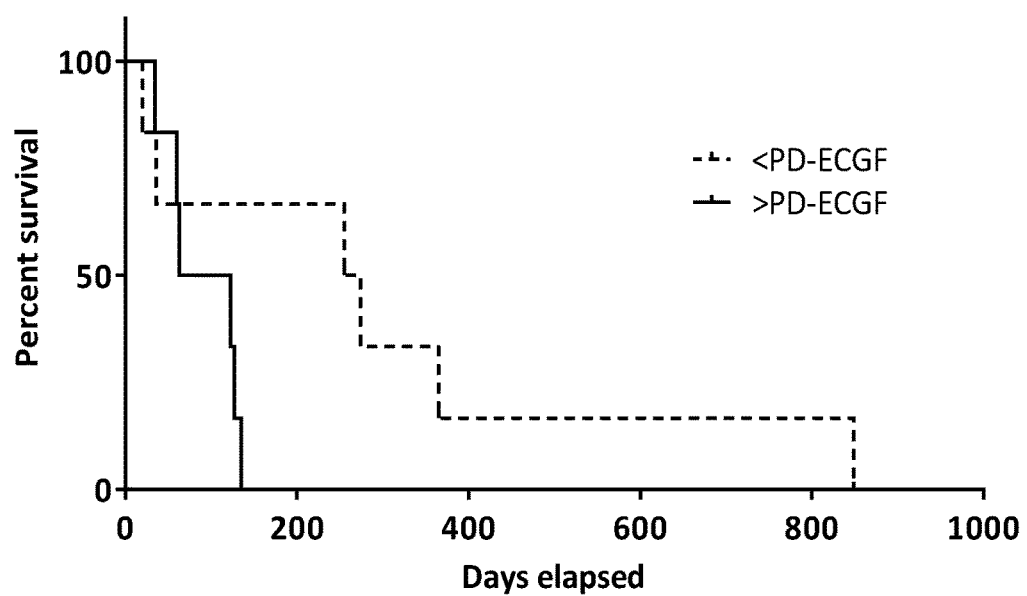
FIG. 10. Kaplan-Meier survival plot of progression free survival in RCC patients related with the plasma levels of PD-ECGF.
Figure 11:
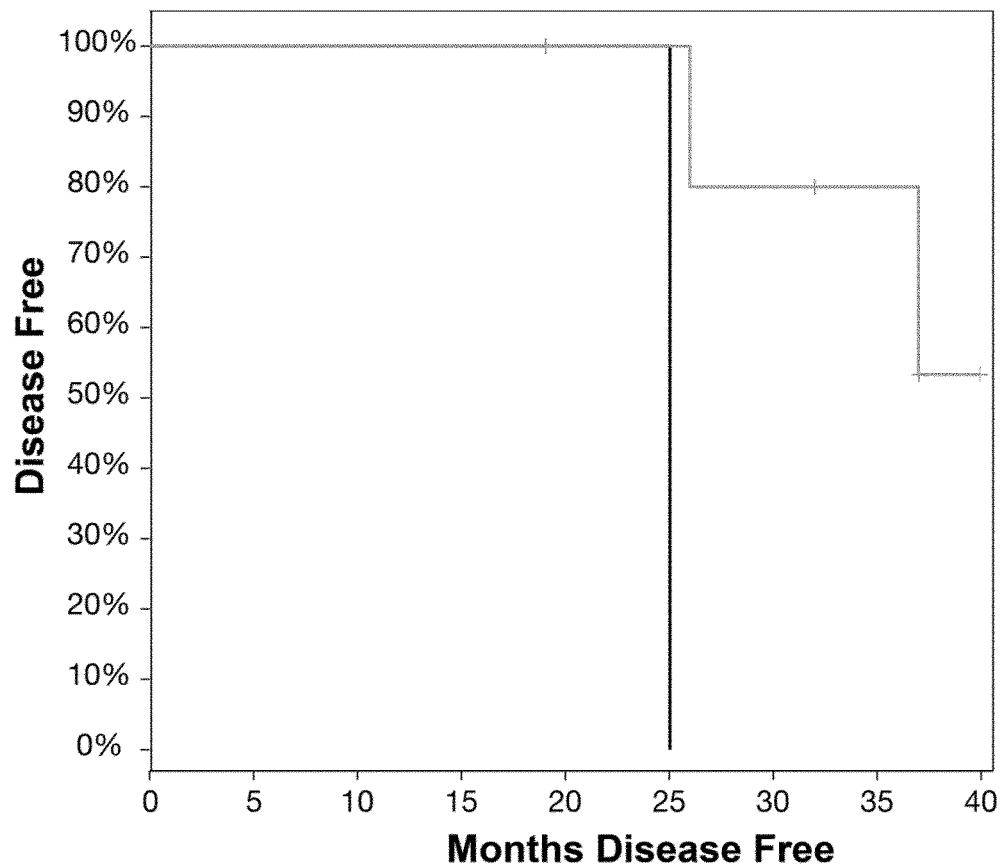
FIG. 11. Kaplan-Meier disease-free survival plot of colorectal adenocarcinoma patients wherein PD-ECGF expression is altered. All complete tumors (7 samples). Reference: Colorectal Adenocarcinoma (TCGA, Provisional).
Figure 12:
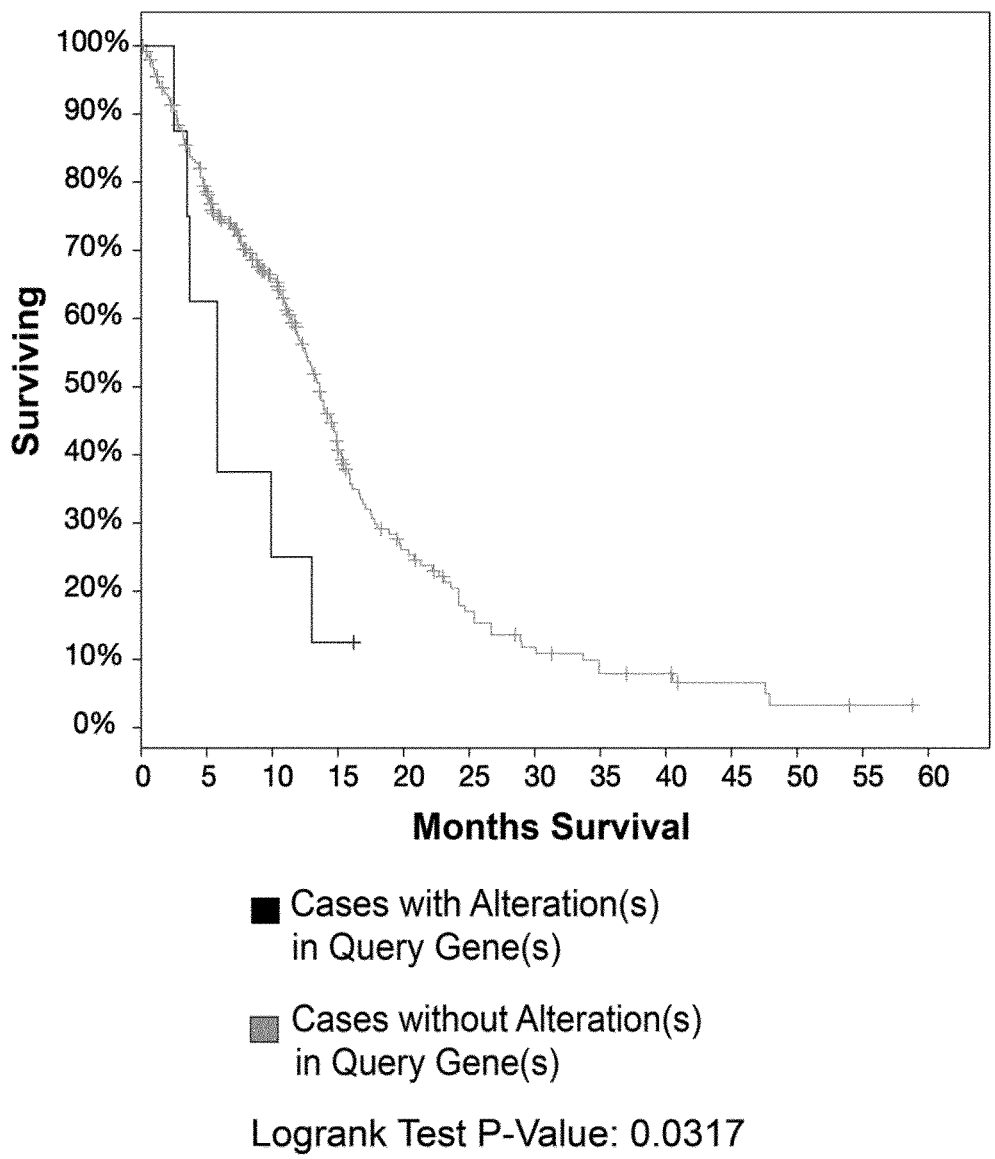
FIG. 12. Kaplan-Meier overall survival plot of glioblastoma patients wherein PD-ECGF expression is altered. All complete tumors (291 samples). Reference: Brennan C W et al., The somatic genomic landscape of glioblastoma. Cell. 2013 Oct. 10; 155(2):462-77.
Figure 13:
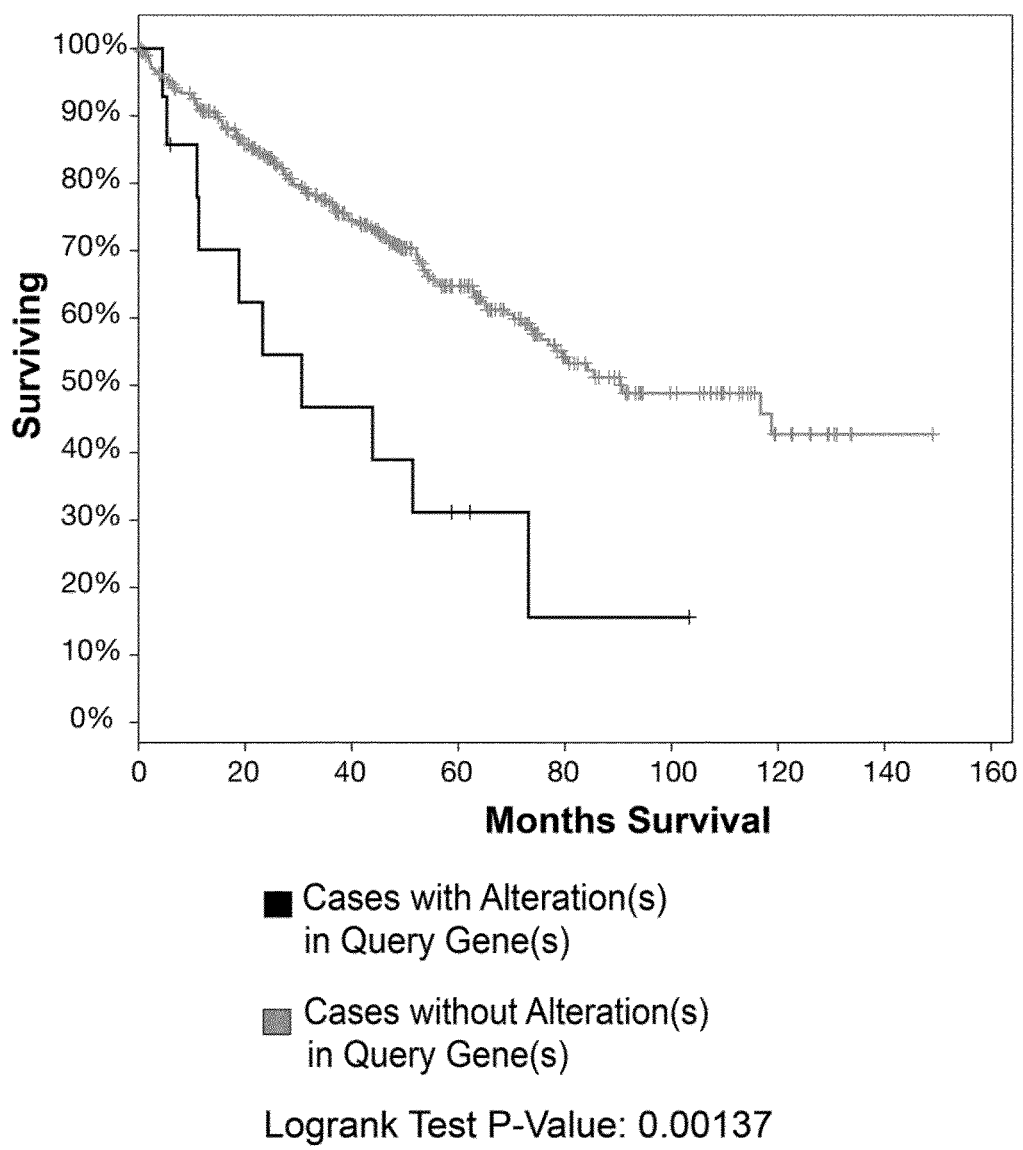
FIG. 13. Kaplan-Meier overall survival plot of kidney renal clear cell carcinoma patients wherein PD-ECGF expression is altered. All complete tumors (413 samples). Reference: Kidney Renal Clear Cell Carcinoma (TCGA, Provisional).
Figure 14:
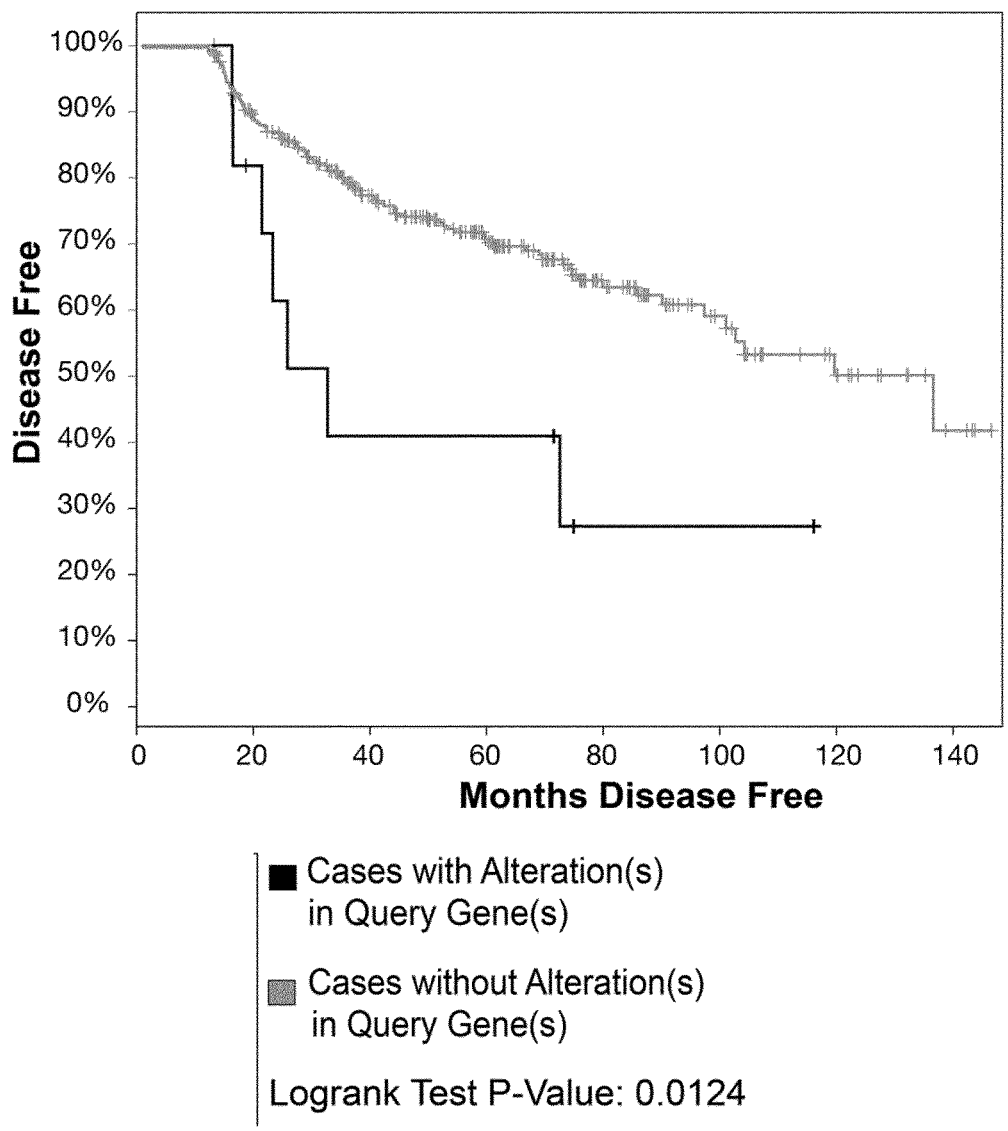
FIG. 14. Kaplan-Meier disease-free survival plot of kidney renal clear cell carcinoma patients wherein PD-ECGF expression is altered. All complete tumors (413 samples). Reference: Kidney Renal Clear Cell Carcinoma (TCGA, Provisional).
Figure 15:
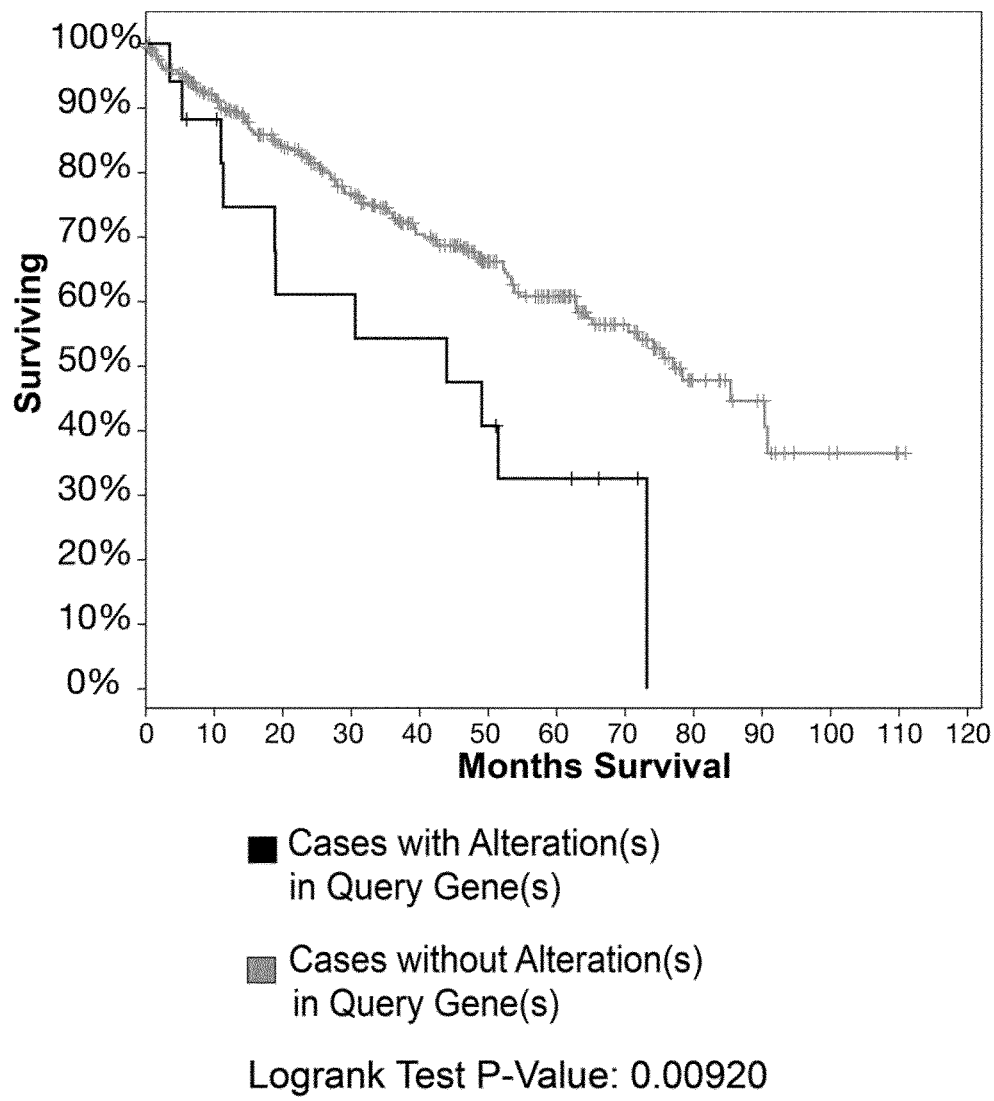
FIG. 15. Kaplan-Meier overall survival plot of kidney renal clear cell carcinoma patients wherein PD-ECGF expression is altered. All complete tumors (392 samples). Reference: Cancer Genome Atlas Research Network. Comprehensive molecular characterization of clear cell renal cell carcinoma. Nature. 2013 Jul. 4; 499(7456):43-9.
Figure 16:
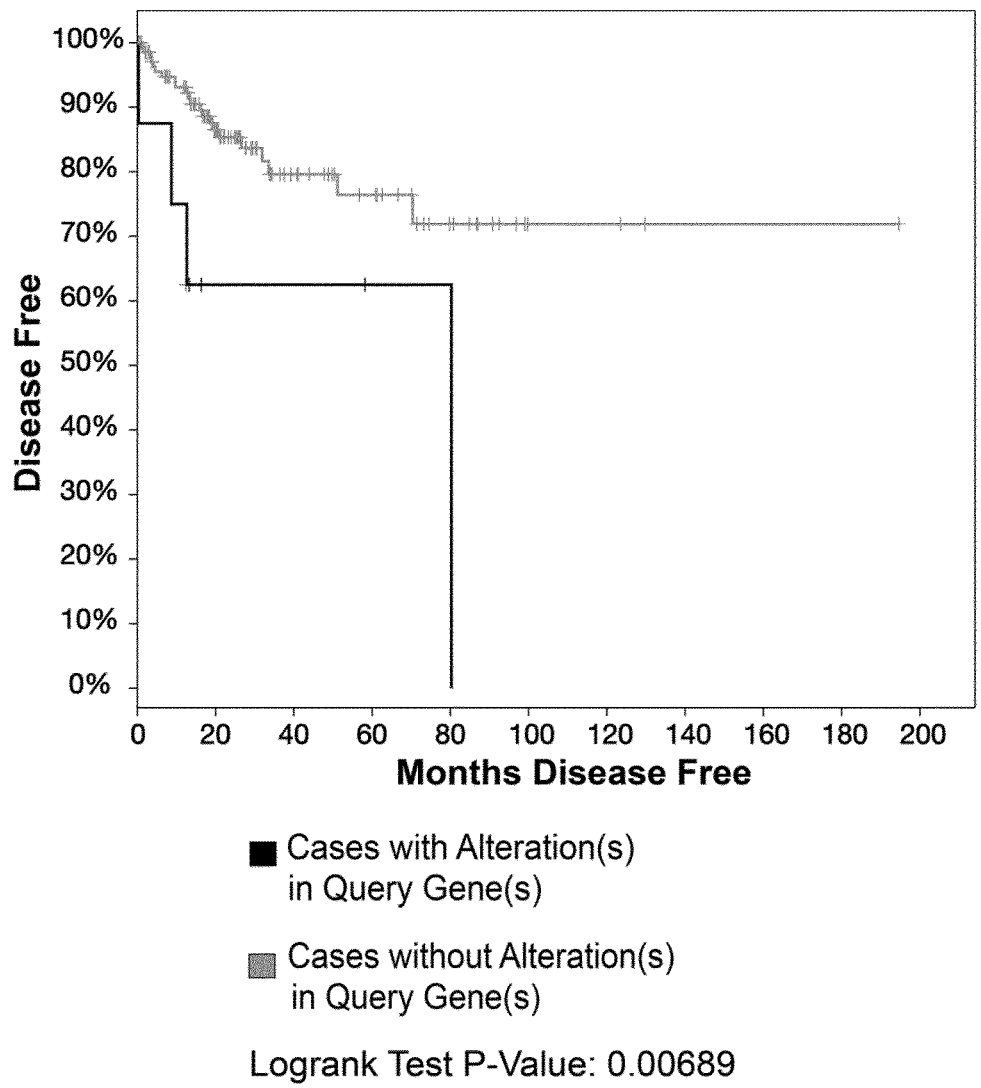
FIG. 16. Kaplan-Meier disease-free survival plot of kidney renal papillary cell carcinoma patients wherein PD-ECGF expression is altered. All complete tumors (161 samples). Reference: Kidney Renal Papillary Cell Carcinoma (TCGA, Provisional).
Figure 17:
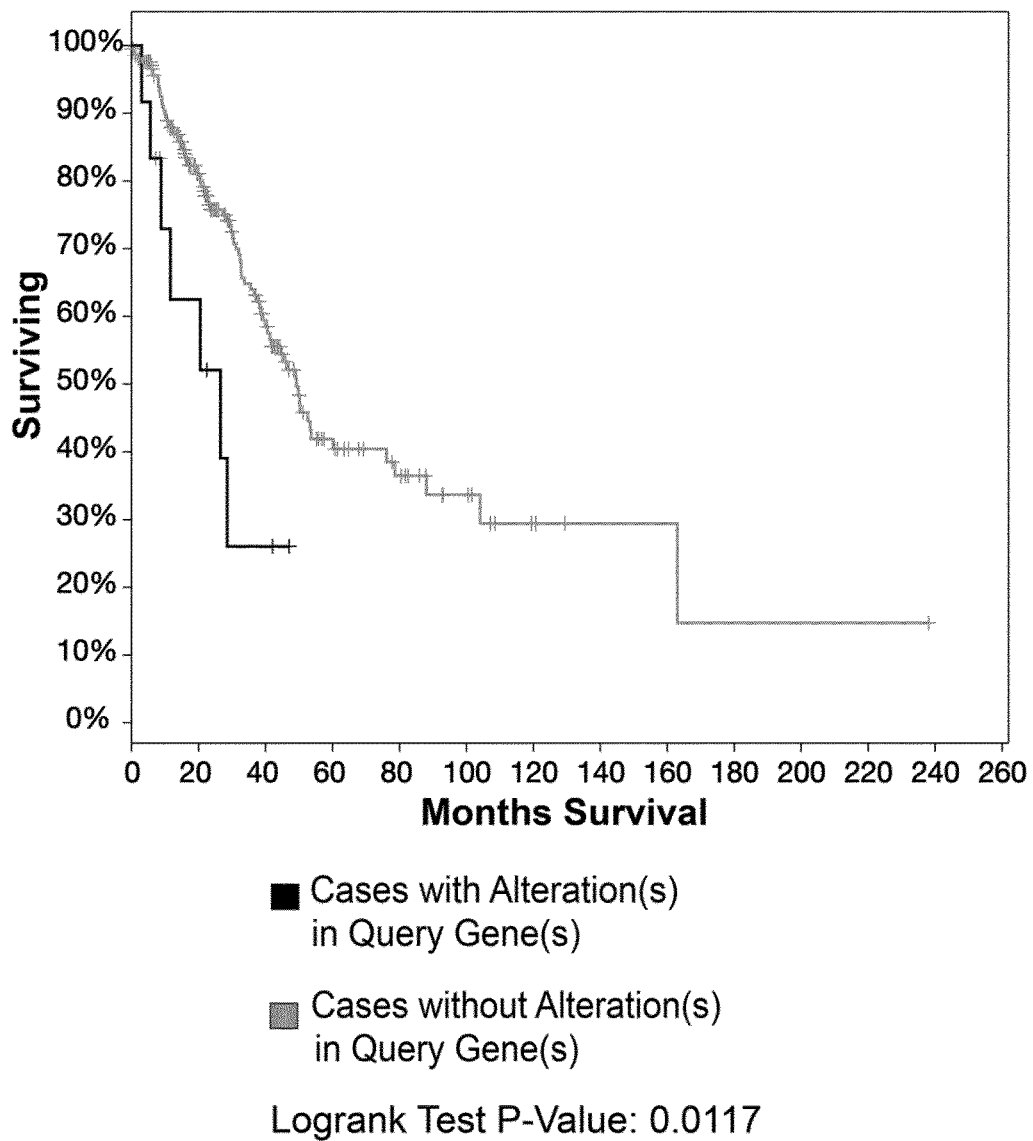
FIG. 17. Kaplan-Meier overall survival plot of lung adenocarcinoma patients wherein PD-ECGF expression is altered. All complete tumors (230 samples). Reference: Lung Adenocarcinoma (TCGA, Provisional).
Figure 18:
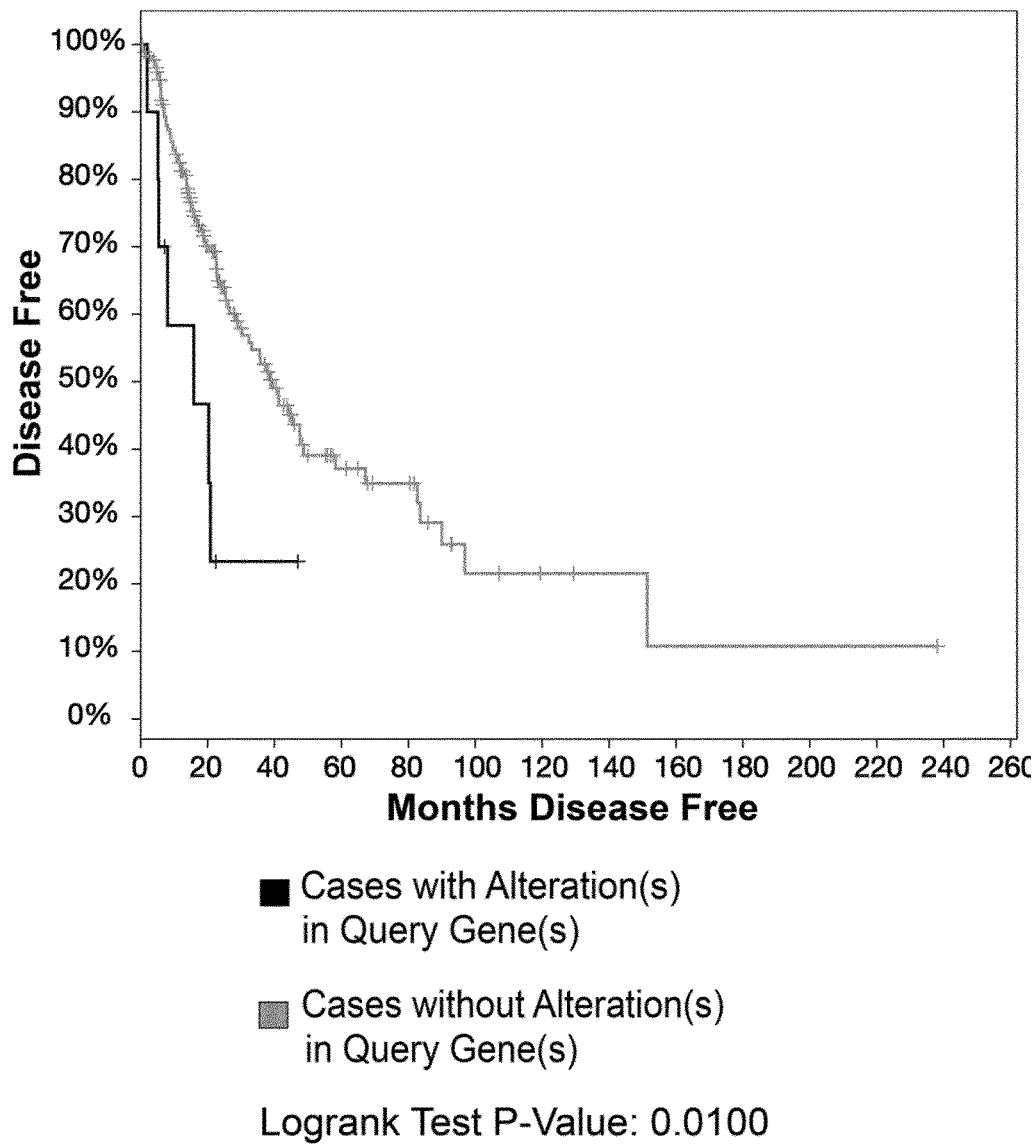
FIG. 18. Kaplan-Meier disease-free survival plot of lung adenocarcinoma patients wherein PD-ECGF expression is altered. All complete tumors (230 samples). Reference: Lung Adenocarcinoma (TCGA, Provisional).
Figure 19:
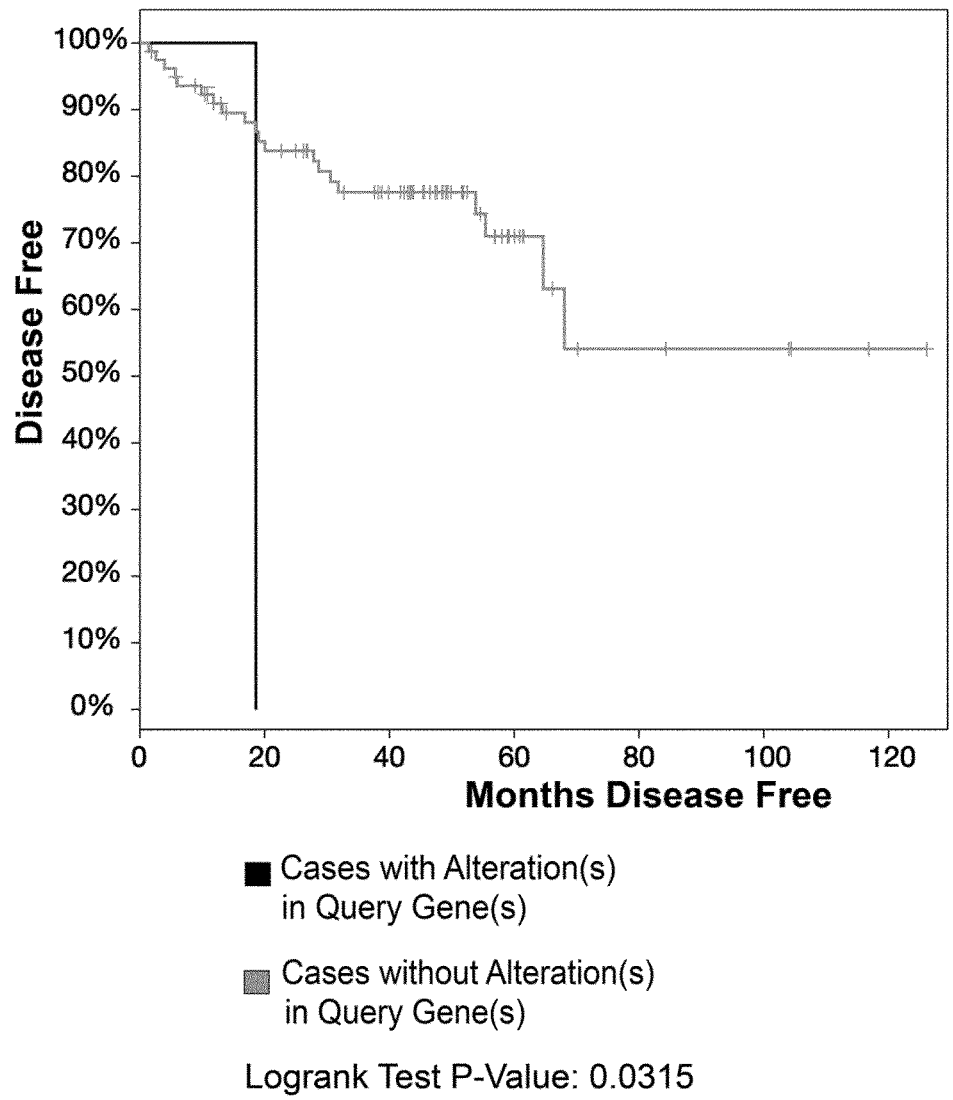
FIG. 19. Kaplan-Meier disease-free survival plot of prostate adenocarcinoma patients wherein PD-ECGF expression is altered. All complete tumors (85 samples). Reference: Taylor B S et al., Integrative genomic profiling of human prostate cancer. Cancer Cell. 2010 Jul. 13; 18(1):11-22.
Figure 20:
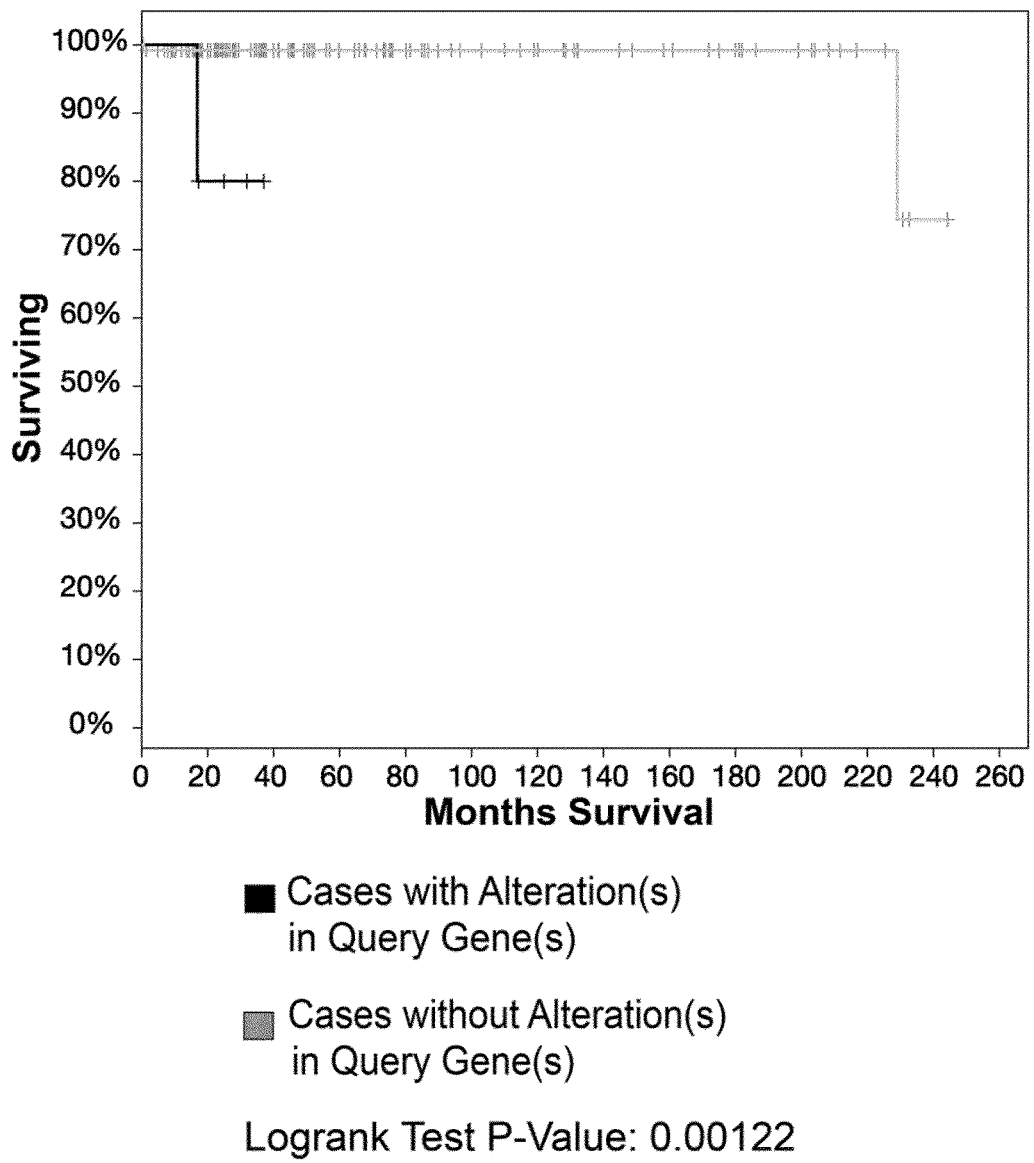
FIG. 20. Kaplan-Meier overall survival plot of testicular germ cell cancer patients wherein PD-ECGF expression is altered. All complete tumors (149 samples). Reference: Testicular Germ Cell Cancer (TCGA, Provisional).
Figure 21:
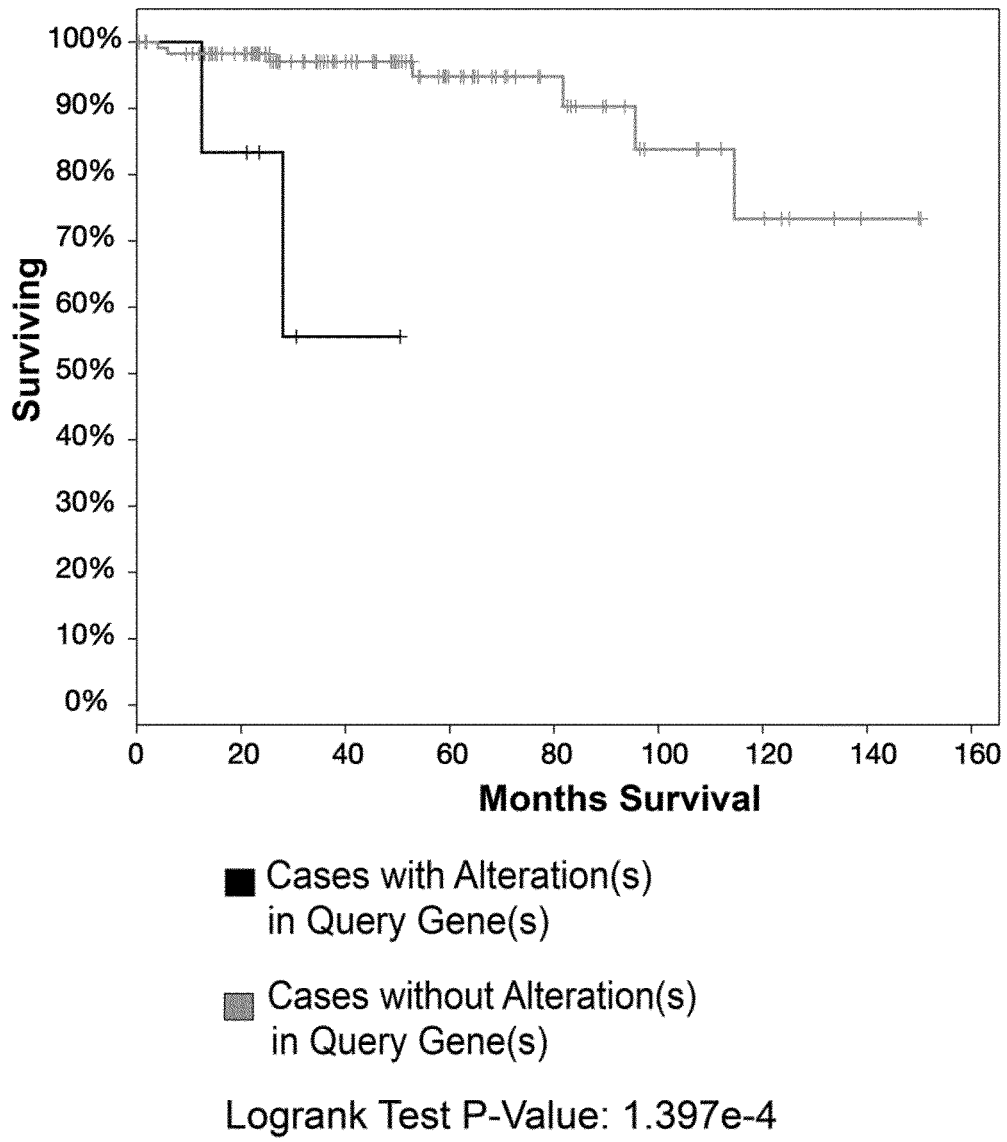
FIG. 21. Kaplan-Meier overall survival plot of thymoma patients wherein PD-ECGF expression is altered. All complete tumors (124 samples). Reference: Thymoma (TCGA, Provisional).
Figure 22:
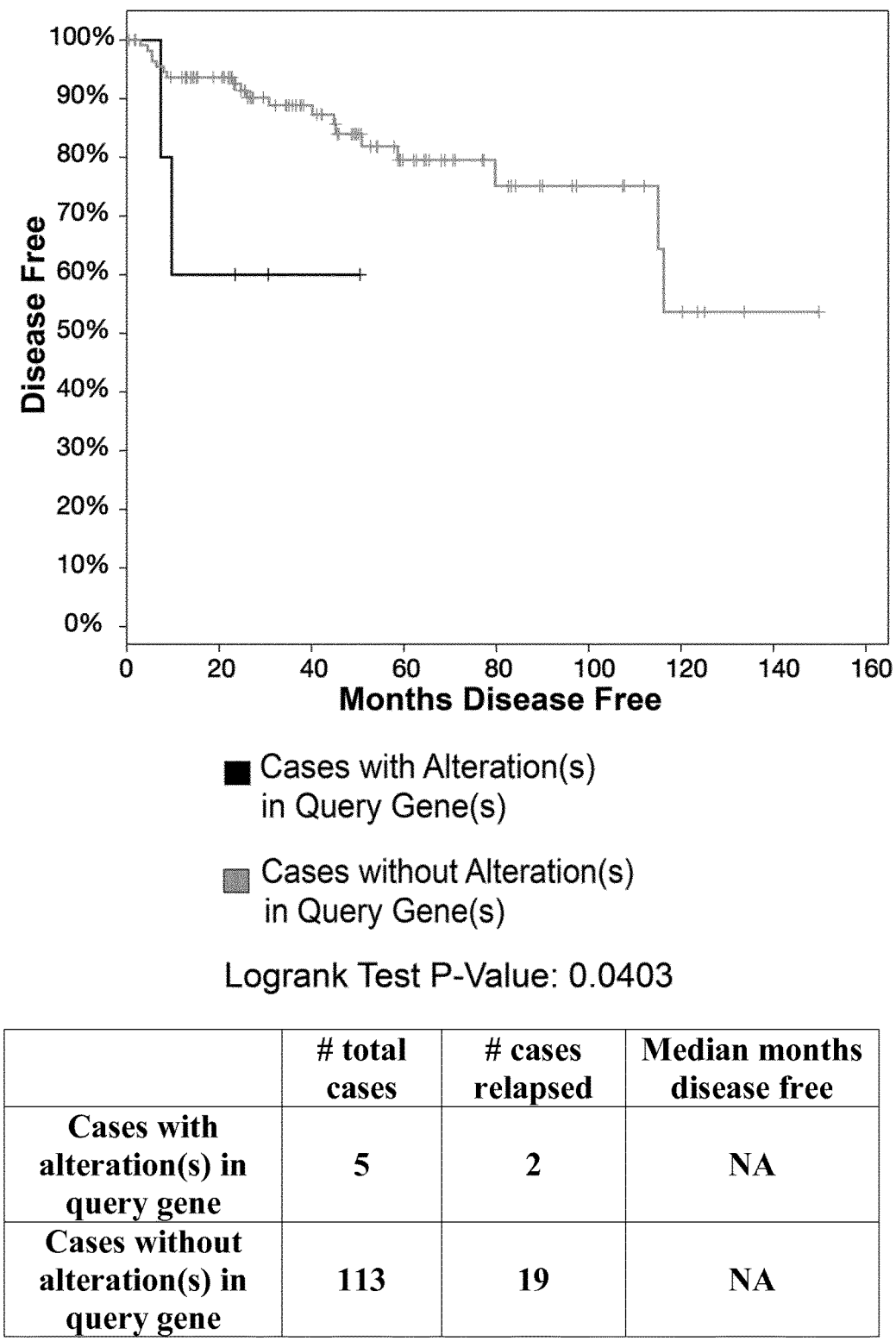
FIG. 22. Kaplan-Meier disease-free survival plot of thymoma patients wherein PD-ECGF expression is altered. All complete tumors (124 samples). Reference: Thymoma (TCGA, Provisional).

Results showed that:
PD-ECGF was evaluated in colorectal cancer plasma samples from 52 patients; there is a significant association between plasma levels of PD-ECGF and risk of early progression represented by a significant hazard ratio for PD-ECGF levels in disease progression in colorectal cancer patients (posterior probability of Hazard ratio was used to evaluate the data, and posterior probability that the hazard ratio be higher than 1 was equal to 0.041, which shows association between tumor progression and PD-ECGF levels) (FIG. 9).
PD-ECGF was evaluated in RCC plasma samples from 14 patients; there is a significant association between higher plasma levels of PD-ECGF and higher risk of early progression in RCC patients (Kaplan-Meier and Log rank (Mantel-Cox) tests, p<0.07). (FIG. 10).
Thus, PD-ECGF expression has potential value in predicting cancer progression in treated patients. These findings support the use of PD-ECGF as a novel biomarker with predictive value of response to treatment for RCC, breast cancer, colorectal cancer and other types of cancer.

Example 4. PD-ECGF Expression Levels and Cancer Prognosis

To analyze the relation between PD-ECGF expression levels and the prognosis of cancer, the inventors generated Kaplan-Meier survival curves based on cancer patients with low or high expression of PD-ECGF by using cBioPortal for Cancer Genomics (www.cbioportal.org) (FIG. A-M).

The following protocol was followed to generate FIGS. 11-23: select "Query" on the home page of the website www.cbioportal.org, select "studies in cancer patients (*)" from Select Cancer Study. In the "Select Genomic Profiles", only select "mRNA Expression z-Scores (RNA Seq V2 RSEM). "Enter Gene set", input "TYMP", and then click "Submit". Oncoprint gives the percentage of alteration (see Table 1 and Table 2 below) and Click "Survival" tab, overall survival Kaplan-Meier Estimate will appear.

TABLE 1

Percentage of PD-ECGF alteration in cancer cell lines

| Studies in cancer cell lines | PD-ECGF (% of alteration) |
| --- | --- |
| Cancer Cell Line Encyclopedia (Novartis/Broad, Nature 2012) All Complete tumors (877 samples) | 12 |
| NCI-60 Cell Lines (NCI, Cancer Res. 2012) All complete samples (60 samples) | 7 |

TABLE 2

Percentage of PD-ECGF alteration in cancer patients

| Studies in cancer patients | PD-ECGF % of alteration |
|---|---|
| Colorectal Adenocarcinoma (TCGA, Provisional) All Complete Tumors (7 samples) | 14% |
| Glioblastoma (TCGA, Nature 2008) All Complete Tumors (91 samples) | 2% |
| Glioblastoma (TCGA, Cell 2013)All Complete Tumors (291 samples) | 3% |
| Stomach Adenocarcinoma (TCGA, Provisional) All Complete Tumors (33 samples) | 3% |
| Kidney Renal Clear Cell Carcinoma (TCGA, Provisional)All Complete Tumors (413 samples) | 4% |
| Kidney Renal Clear Cell Carcinoma (TCGA, Nature 2013) All Complete Tumors (392 samples) | 5% |
| Kidney Renal Papillary Cell Carcinoma (TCGA, Provisional)All Complete Tumors (161 samples) | 5% |
| Lung Adenocarcinoma (TCGA, Provisional)All Complete Tumors (230 samples) | 6% |
| Prostate Adenocarcinoma (MSKCC, Cancer Cell 2010) All Complete Tumors (85 samples) | 2% |
| Prostate Adenocarcinoma (TCGA, Provisional) All Complete Tumors (332 samples) | 4% |
| Testicular Germ Cell Cancer (TCGA, Provisional) All Complete Tumors (149 samples) | 4% |
| Thymoma (TCGA, Provisional) All Tumors (124 samples) | 5% |
| Thyroid Carcinoma (TCGA, Provisional) All Complete Tumors (397 samples) | 6% |
| Papillary Thyroid Carcinoma (TCGA, Cell 2014) All Complete Tumors (388 samples) | 6% |

Figure 23:
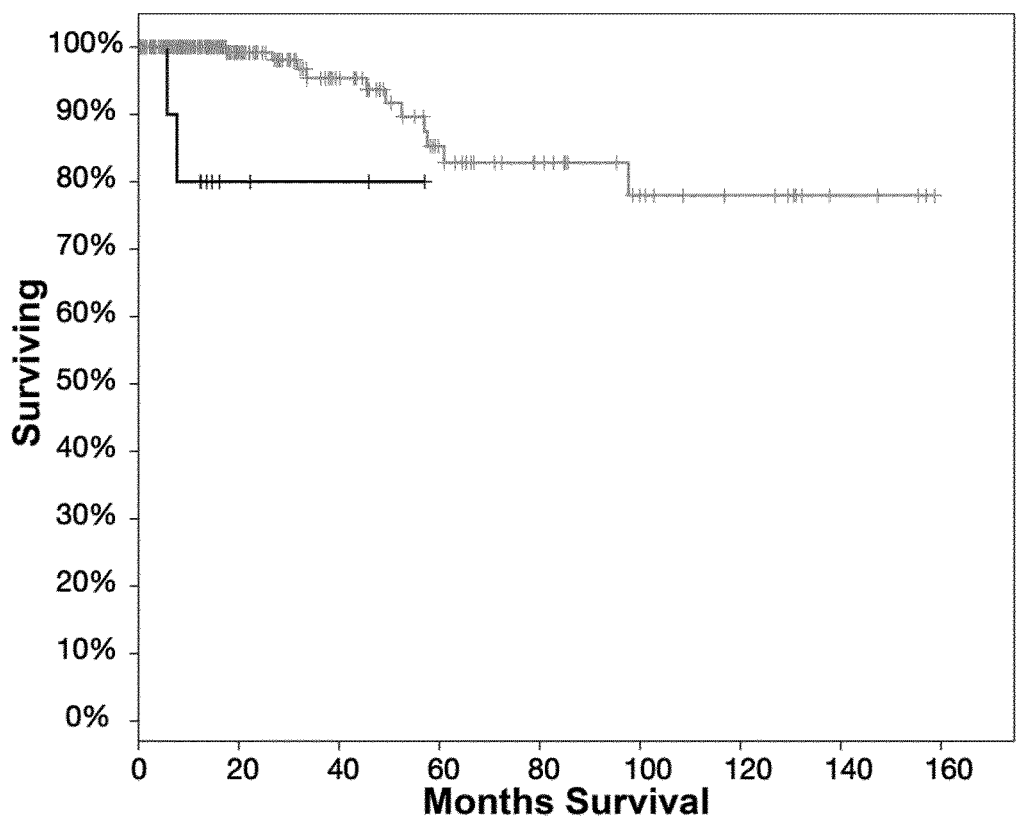
FIG. 23. Kaplan-Meier overall survival plot of papillary thyroid carcinoma patients wherein PD-ECGF expression is altered. All complete tumors (388 samples). Reference: Cancer Genome Atlas Research Network. Integrated genomic characterization of papillary thyroid carcinoma. Cell. 2014 Oct. 23; 159(3):676-90.

Results showed the following:
- colorectal adenocarcinoma cases with PD-ECGF alteration have worse disease free survival than cases without PD-ECGF alteration (FIG. 11),
- glioblastoma cases with PD-ECGF alteration have worse overall survival than cases without PD-ECGF alteration (FIG. 12),
- kidney renal clear cell carcinoma cases with PD-ECGF alteration have worse overall survival than cases without PD-ECGF alteration (FIG. 13),
- kidney renal clear cell carcinoma cases with PD-ECGF alteration have worse disease free survival than cases without PD-ECGF alteration (FIG. 14),
- kidney renal clear cell carcinoma cases with PD-ECGF alteration have worse overall survival than cases without PD-ECGF alteration (FIG. 15),
- kidney renal papillary cell carcinoma cases with PD-ECGF alteration have worse disease free survival than cases without PD-ECGF alteration (FIG. 16),
- lung adenocarcinoma cases with PD-ECGF alteration have worse overall survival than cases without PD-ECGF alteration (FIG. 17),
- lung adenocarcinoma cases with PD-ECGF alteration have worse disease free survival than cases without PD-ECGF alteration (FIG. 18),
- prostate adenocarcinoma cases with PD-ECGF alteration have worse disease free survival than cases without PD-ECGF alteration (FIG. 19),
- testicular germ cell cancer cases with PD-ECGF alteration have worse overall survival than cases without PD-ECGF alteration (FIG. 20),
- thymoma cases with PD-ECGF alteration have worse overall survival than cases without PD-ECGF alteration (FIG. 21),
- thymoma cases with PD-ECGF alteration have worse disease free survival than cases without PD-ECGF alteration (FIG. 22), and
- papillary thyroid carcinoma cases with PD-ECGF alteration have worse overall survival than cases without PD-ECGF alteration (FIG. 23).

The invention claimed is:

1. A method for providing an anti-angiogenic treatment to a subject suffering from cancer, wherein said anti-angiogenic treatment is not doxorubicin or interferon therapy and wherein the cancer is renal cell carcinoma or colorectal cancer, the method comprising:
   (i) obtaining a sample from the subject, wherein the sample is a tissue sample or a biological fluid sample, and wherein the tissue sample is a sample from a tumor or wherein the biological fluid sample is a sample of blood, serum or plasma;
   (ii) determining the level of PD-ECGF in the sample from said subject;
   (iii) comparing the level obtained in (ii) to a reference value, and
   (iv) administering an anti-angiogenic treatment to a subject having a decreased level of PD-ECGF when compared to the reference value, wherein said anti-angiogenic treatment is not doxorubicin or interferon therapy.

2. A method according to claim 1, wherein response is measured as early progression of cancer.

3. A method according to claim 1, wherein the anti-angiogenic treatment is initiated after the determination of the levels of PD-ECGF.

4. The method of claim 1, wherein the tumor is the primary tumor or a metastasis.

5. The method according to claim 1, wherein the level of PD-ECGF determined is the PD-ECGF protein level.

6. The method according to claim 5, wherein the PD-ECGF protein level is determined by immunohistochemistry, by ELISA, or by western blot.

7. The method according to claim 1, wherein the anti-angiogenic treatment comprises an anti-VEGF agent.

8. The method according to claim 7, wherein the anti-VEGF agent is an anti-VEGF antibody.

9. The method according to claim 8, wherein the anti-VEGF agent is bevacizumab.

10. The method according to claim 1, wherein the anti-angiogenic treatment comprises an agent which inhibits the tyrosine kinases stimulated by VEGF.

11. The method according to claim 10, wherein the agent which inhibits the tyrosine kinases stimulated by VEGF is sunitinib.

12. The method according to claim 1, wherein the anti-angiogenic treatment comprises a VEGFR2 blocking antibody.

13. The method according to claim 12, wherein the VEGFR2 blocking antibody is DC101.

14. The method according to claim 1 wherein the cancer is renal cell carcinoma.

15. The method according to claim 1 wherein the cancer is colorectal cancer.

* * * * *